US011561135B2

(12) United States Patent
Putterman et al.

(10) Patent No.: US 11,561,135 B2
(45) Date of Patent: Jan. 24, 2023

(54) ARTIFICIAL INTELLIGENCE (AI) PROCEDURE FOR NORMALIZING THERMAL SKIN TEMPERATURE TO BODY TEMPERATURE

(71) Applicant: Kogniz, Inc., Mill Valley, CA (US)

(72) Inventors: Jed Putterman, Mill Valley, CA (US); Daniel Putterman, Mill Valley, CA (US); Bill Klein, Montreal (CA)

(73) Assignee: Kogniz, Inc., Mill Valley, CA (US)

( * ) Notice: Subject to any disclaimer, the term of this patent is extended or adjusted under 35 U.S.C. 154(b) by 248 days.

(21) Appl. No.: 16/950,692

(22) Filed: Nov. 17, 2020

(65) Prior Publication Data

US 2022/0157146 A1    May 19, 2022

(51) Int. Cl.
*G01J 5/00* (2022.01)
*G06T 7/70* (2017.01)
*A61B 5/00* (2006.01)
*A61B 5/01* (2006.01)
*G06V 10/143* (2022.01)
*G06V 40/50* (2022.01)
(Continued)

(52) U.S. Cl.
CPC .......... *G01J 5/0025* (2013.01); *A61B 5/0008* (2013.01); *A61B 5/0015* (2013.01); *A61B 5/0077* (2013.01); *A61B 5/01* (2013.01); *A61B 5/746* (2013.01); *G06T 7/70* (2017.01); *G06V 10/143* (2022.01); *G06V 40/166* (2022.01); *G06V 40/50* (2022.01); *A61B 2562/0271* (2013.01); *G06T 2207/20084* (2013.01); *G06T 2207/30201* (2013.01); *G06V 40/15* (2022.01)

(58) Field of Classification Search
CPC .... G01J 5/0025; A61B 5/0008; A61B 5/0015; A61B 5/0077; A61B 5/01; A61B 5/746; A61B 2562/0271; G06T 7/70; G06T 2207/20084; G06T 2207/30201; G06V 10/143; G06V 40/166; G06V 40/50; G06V 40/15
See application file for complete search history.

(56) References Cited

U.S. PATENT DOCUMENTS 9,759,632 B2 * 9/2017 Trescott ................. G01K 13/02
10,227,063 B2 * 3/2019 Abreu ..................... B60T 7/14
(Continued)

*Primary Examiner* — Mohamed Barakat
(74) *Attorney, Agent, or Firm* — Holland & Hart LLP

(57) ABSTRACT

Methods, systems, and devices for data processing and artificial intelligence (AI) techniques are described. A system may support person detection using an optical camera and temperature detection using a thermal sensor. The thermal sensor may determine a temperature reading corresponding to a tracker for a specific detected person. A processing device may update a current temperature for the tracker based on the temperature reading and may add the updated current temperature to a baseline. For example, the processing device may use AI techniques to manage one or more baselines supporting handling of differences and changes in ambient temperatures. The processing device may determine that the current temperature for the tracker satisfies an alert threshold and may trigger an alert procedure. For example, the processing device may use an active baseline to correct the current temperature from a skin temperature to a body temperature for comparison to a fever detection threshold.

19 Claims, 10 Drawing Sheets

(51) Int. Cl.
 *G06V 40/16* (2022.01)
 *G06V 40/10* (2022.01)

(56) References Cited

U.S. PATENT DOCUMENTS

| | | | |
|---|---|---|---|
| 10,909,835 B1* | 2/2021 | Singh | G01J 5/0806 |
| 2017/0156594 A1* | 6/2017 | Stivoric | A61B 5/0008 |
| 2020/0364384 A1* | 11/2020 | Li | G06F 30/17 |
| 2021/0378520 A1* | 12/2021 | Rao | A61B 5/01 |

* cited by examiner

ARTIFICIAL INTELLIGENCE (AI) PROCEDURE FOR NORMALIZING THERMAL SKIN TEMPERATURE TO BODY TEMPERATURE

FIELD OF TECHNOLOGY

The present disclosure relates generally to data processing and artificial intelligence (AI) systems, and more specifically to an AI procedure for normalizing thermal skin temperature to body temperature.

BACKGROUND

Some environments 13 such as office buildings, stores, schools, or other environments—implement temperature screening for individuals entering the environment. The temperature screening may be used to detect if a person has a fever, potentially indicating that the person is sick (e.g., infected with a virus that may be transmitted to others in the environment). Such temperature screenings are often performed as quick, efficient checks to ensure people with fevers (e.g., body temperatures above 38° Celsius (C) or 100.4° Fahrenheit (F)) are not permitted to enter the environment. The temperature screenings may be performed by a thermal sensor to avoid physical contact.

However, using a thermal sensor may introduce significant error into the temperature readings. For example, the thermal sensor may measure skin temperature, as opposed to body temperature. While body temperature may accurately indicate whether a person's temperature indicates a fever, skin temperature may fluctuate significantly based on the ambient temperature. For example, a thermal sensor may measure a significantly different temperature for a person entering a building from an outdoor temperature of 32° F. than for a person entering a building from an outdoor temperature of 100° F., regardless of each person's body temperature. Such fluctuations in skin temperature based on ambient temperature may result in inaccurate temperature screenings, potentially leading to people with fevers being measured below a fever threshold and being allowed to enter an environment.

DETAILED DESCRIPTION

Figure 1:
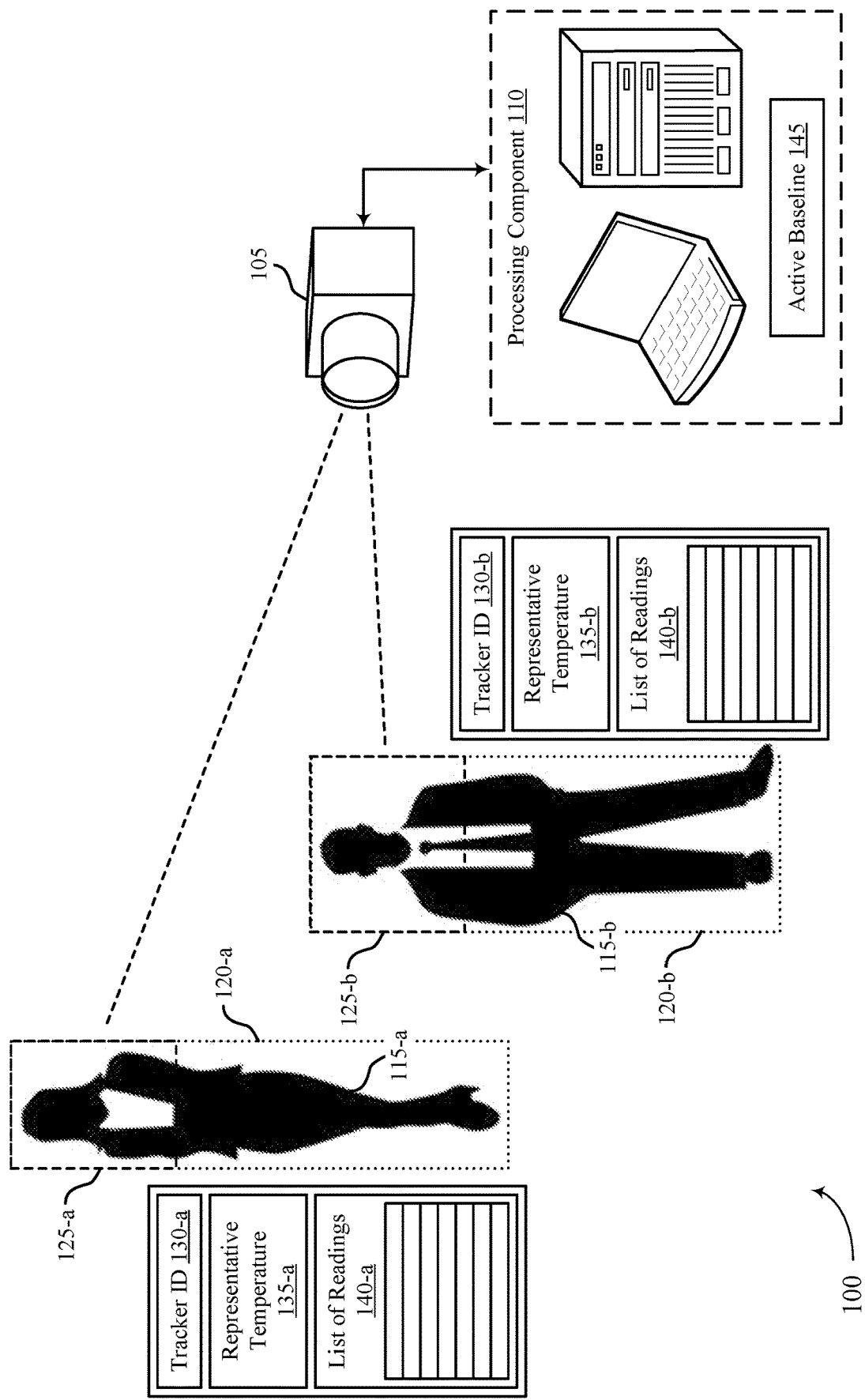
FIG. 1 illustrates an example of a system for temperature detection that supports an artificial intelligence (AI) procedure for normalizing thermal skin temperature to body temperature in accordance with aspects of the present disclosure.

An environment, such as the entrance to a building, may implement a system for temperature screening. The temperature screening may allow the system to detect people entering the environment with a fever and trigger an alert based on the fever detection. In some systems, the temperature screening may be performed by a thermal sensor to avoid physical contact. However, using a thermal sensor may introduce significant errors into the temperature readings. For example, the thermal sensor may measure skin temperature which may fluctuate significantly based on an ambient temperature. If a person enters the environment from a first ambient temperature (e.g., an outdoor ambient temperature) different from a second ambient temperature for the environment (e.g., an indoor ambient temperature), the temperature readings for the person's skin temperature may be affected by the first ambient temperature. Accordingly, the temperature readings from the thermal sensor may fail to accurately indicate the person's body temperature, potentially allowing a person with a fever to enter the environment without triggering an alert. Furthermore, the ambient temperature affecting people entering the environment and the ambient temperature affecting the thermal sensor in the environment may dynamically change (e.g., due to changes in weather, time of day, or other factors), further reducing the system's ability to accurately determine body temperatures from the thermal sensor's temperature readings.

As described herein, a system may implement artificial intelligence (AI) techniques to support normalizing thermal skin temperatures to body temperatures. For example, a thermal sensor may measure thermal skin temperatures, while body temperatures may be used for fever detection. Because the conversion from a thermal skin temperature to a body temperature may depend on multiple factors, the system may implement one or more neural networks, baseline and clustering techniques, or a combination thereof to dynamically determine accurate conversions and support reliable fever detection based on thermal sensor temperature readings.

The system may support person detection using an optical camera and temperature detection using a thermal sensor (e.g., including a microbolometer). The thermal sensor may determine a temperature reading corresponding to a tracker identifier (ID), where the tracker ID indicates a tracker for a specific person detected in an environment. A processing device may update a current temperature for the tracker based on the temperature reading and may add the updated current temperature to a baseline (e.g., an active baseline, an inactive baseline, or a new baseline). For example, the processing device may use AI techniques to build and maintain one or more baselines supporting conversions from skin temperature readings to body temperatures. The system may dynamically update the baselines as people are detected in the environment throughout the day to both account for the difference between the ambient temperature in the environment and an external ambient temperature and account for dynamic changes to one or both of these ambient temperatures.

The processing device may determine that the current temperature for the tracker satisfies an alert threshold for the active baseline and may trigger an alert procedure. For example, the processing device may use the active baseline to correct the current temperature from a skin temperature to a body temperature and may compare the body temperature (e.g., a "corrected" temperature) to a fever detection threshold. In some cases, if the corrected temperature exceeds the fever detection threshold, the processing device may implement a checking procedure to delay sending an alert and perform multiple measurements to confirm the temperature readings. If the checking procedure confirms that a person has a corrected temperature above the fever detection threshold, the processing device may send an alert to indicate the person with the detected fever.

Aspects of the disclosure are initially described in the context of a system for temperature detection. Additional aspects of the disclosure are described with reference to temperature reading procedures, tracker and baseline management procedures, and a process flow. Aspects of the disclosure are further illustrated by and described with reference to apparatus diagrams, system diagrams, and flowcharts that relate to an AI procedure for normalizing thermal skin temperature to body temperature.

FIG. 1 illustrates an example of a system 100 for temperature detection that supports an AI procedure for normalizing thermal skin temperature to body temperature in accordance with aspects of the present disclosure. The system 100 may support temperature screening for an environment using a thermal sensor 105, which may be connected to or otherwise include a processing component 110. The thermal sensor 105 may be coupled to or aligned with an optical camera for person detection. The optical camera may autonomously detect a person 115 entering the environment and may detect the person's face (e.g., based on detecting a first set of pixels 120 corresponding to a person's body and a second set of pixels 125 in which to scan for a face). The thermal sensor 105 may measure temperature readings for a person's face, and the processing component 110, using a correction algorithm, may translate the measured skin temperature into a body temperature for the person 115. The processing component 110 may determine whether to trigger an alert based on whether the corrected body temperature satisfies (e.g., exceeds) a fever threshold.

As a person 115 enters the environment, the person's skin temperature may be based on the ambient temperature external to the environment. For example, the person 115 may enter a building from the outside. As such, the person's skin temperature may be based on the ambient temperature outdoors, while the thermal sensor 105 may experience a different ambient temperature (e.g., an indoor ambient temperature for the building). Accordingly, a skin temperature for the person 115 obtained by the thermal sensor 105 may be dependent on a different ambient temperature than the thermal sensor 105 can detect. Additionally, the ambient temperature around the thermal sensor 105 and the ambient temperature that affected the person's skin temperature may both change dynamically.

Some other systems may require a person to acclimate to the ambient temperature in an environment monitored by a thermal sensor. For example, a person may wait a period of time (e.g., up to thirty minutes) so that the person's skin temperature is dependent on the ambient temperature around the thermal sensor, which the thermal sensor may account for (e.g., based on a calibration procedure). However, in many environments, waiting for a person to acclimate to a new ambient temperature before obtaining the person's temperature may not be feasible. For example, buildings with heavy traffic, small waiting areas, specific appointment times, or the like may not support such an acclimation process. However, not having a person acclimate to the temperature may result in skin temperature readings that result in false negatives or false positives when performing fever detection. For example, a thermal sensor may detect a skin temperature reading for a person that exceeds a fever threshold based on the person entering a building from a hot, sunny day, even if the person does not actually have a fever. Similarly, the thermal sensor may detect a skin temperature reading for a person that does not exceed a fever threshold based on the person entering the building from a cold environment, potentially allowing a person with a fever to escape detection. Yet other systems may implement thermometers or other means to measure body temperature, rather than skin temperature. However, such means may risk spreading illnesses through physical contact and may be expensive and wasteful (e.g., using disposable thermometers) or risk contamination (e.g., using reusable thermometers).

In contrast, the system 100 may implement a set of baselines, including an active baseline 145, to account for differences and changes in ambient temperatures. In this way, the thermal sensor 105 may obtain temperature readings for a person's face that are useful in determining an accurate body temperature measurement (e.g., without the person 115 acclimating to the ambient temperature around the thermal sensor 105). Such accurate body temperatures may allow the system 100 to determine whether a person 115 entering the environment has a fever (or is expected to have a fever based on the person's body temperature). If a person 115 with a fever is detected, the thermal sensor 105, the processing component 110, or a combination thereof may trigger an alert, for example, to stop the person 115 from entering further into a building. Such a process may significantly reduce the risk of allowing contagious people into an environment in which they can potentially spread a virus, as the system 100 may accurately identify such people using a thermal sensor 105 and prompt these people to refrain from entering the environment.

The system 100 may implement an optical camera in conjunction with the thermal sensor 105. The optical camera may be described in more detail herein with reference to FIG. 2. The optical camera may be an example of a red, green, and blue (RGB) image sensor and may capture a video of the environment (e.g., an entrance to a building). To reduce the processing involved in detecting a person's face, the optical camera may first detect a body and may detect a face based on the detected body. In this way, the optical camera may refrain from searching for a small image (e.g., a face) in a large image (e.g., the full view of the optical camera). Instead, the optical camera may detect motion between frames in the video stream to determine if a body may be present in the view of the optical camera. For example, the optical camera, the processing component 110, or a combination thereof may process the video stream from the optical camera to analyze the video frame-by-frame (e.g., by decoding the video stream, for example, for an H.264 video stream or an H.265 video stream, or by receiving the frames directly). The processing component 110 may implement a neural network (e.g., a recurrent neural network (RNN)) or another technique to identify state changes across frames (e.g., consecutive frames, periodic frames). Based on the state changes, the optical camera may detect motion and determine if the motion corresponds to a person's body, for example, using another neural network.

The optical camera may detect multiple bodies in a frame and may track the bodies across a set of frames (e.g., using one or more RNNs) according to multiple trackers associated with respective tracker IDs 130. The system 100 (e.g., the optical camera, the processing component 110, or both) may assign a unique tracker ID 130 to each body detected in the frame. The system 100 may use such tracker IDs 130 to manage temperature information for multiple people entering and leaving the environment. In some examples, the processing component 110 may maintain a tracker in memory for a threshold amount of time after the body is not detected in case the body is detected again (e.g., if a person quickly reenters the view of the optical camera, if the person is temporarily obscured from the optical camera, if the optical camera fails to detect the person for a few frames). In this way, the processing component 110 may not assign a new tracker ID 130 to a person who already corresponds to a recently tracked tracker ID 130.

If the optical camera detects a person 115, the system 100 (e.g., the optical camera, the processing component 110, or both) may determine a first set of pixels 120 approximately corresponding to the person's body. The system 100 may use the first set of pixels 120 to simplify the facial detection procedure by limiting the area in which to search for a face to a second set of pixels 125. The second set of pixels 125 may be based on the first set of pixels 120. For example, the second set of pixels 125 may correspond to the upper third of the first set of pixels 120. The system 100 may use a neural network (e.g., a convolutional neural network, such as an 18-layer model) to detect a face in the second set of pixels 125 corresponding to the upper third of an already detected body. The neural network may be trained on data based on searching in a specific area for a face (e.g., the top-third area of a person 115 detection box). In some examples, the system 100 may implement a first detection phase to detect a face in the environment and may implement a second classification phase to classify one or more aspects of the face (e.g., whether the face is wearing glasses, a hat, a mask, or corresponds to another classification).

The system 100 may implement the thermal sensor 105 to determine temperature information for a detected face. In some cases, the system 100 may align the thermal sensor 105 with the optical camera to determine a combined thermal image (e.g., where thermal information is overlaid over an RGB image of an RGB camera). Aligning the thermal sensor 105 with the optical camera may involve determining a distance from the optical camera to the detected face, performing multiple distance measurements, temperature measurements, or both, and determining a pixel alignment between the thermal sensor 105 and the optical camera. As such, the system 100 (e.g., the processing component 110) may determine one or more thermal pixels for the thermal sensor 105 that are equivalent to one or more RGB pixels from the detected face for the optical camera.

In some examples, the optical camera and the thermal sensor 105 may use different frame rates. In a specific example, the optical camera may support a frame rate of 30 to 60 frames per second, while the thermal sensor 105 may support a frame rate of 9 frames per second. As such, the system 100 may perform person tracking and thermal detections at different rates. For example, the optical camera may track a body at a frame rate of 30 to 60 frames per second, while the thermal sensor 105 may perform thermal detections at 9 frames per second for an identified person's face. In some examples, such a process may support storing 9 temperature readings per second for each tracker in the view of the cameras (e.g., the optical camera and the thermal sensor 105).

The thermal sensor 105 may obtain temperature readings from the detected faces. In some cases, the temperature readings may be in Kelvin (K) and may be converted to Celsius (C) or Fahrenheit (F). In some examples, the thermal sensor 105, the optical camera, the processing component 110, or some combination thereof may determine a distance from the thermal sensor 105 to a face. For example, the system 100 may determine the distance based on a stereoscopic sensor or an estimation based on the face's size in the optical camera's view. The thermal sensor 105 may perform temperature readings when the face is a specific distance range from the thermal sensor 105 (e.g., 6 feet to 18 feet). In some cases, the thermal sensor 105, the processing component 110, or a combination thereof may apply an initial correction to the temperature readings based on the distance (e.g., because temperature readings for an object may change slightly based on the distance between the thermal sensor 105 and the object). The thermal sensor 105 may obtain temperature readings from multiple parts of each face and may store each of the temperature readings or determine a single temperature reading to store for the face for each frame. The temperature readings may be stored as a list of readings 140 in memory for each tracker ID 130. Additionally, the processing component 110 may determine a representative temperature 135 for each tracker ID based on the list of readings 140. The representative temperature 135 may correspond to a detected skin temperature for a person 115.

To convert from a representative temperature 135 (e.g., corresponding to a skin temperature) to a corrected temperature (e.g., corresponding to a body temperature), the processing component 110 may use an active baseline 145. For example, the processing component 110 may perform clustering to manage a set of baselines, including an active baseline 145, one or more inactive baselines, or a combination thereof. In some cases, the processing component 110 may perform clustering at the tracker-level (e.g., to determine whether temperature readings for a specific person 115 are consistent) and at the group-level (e.g., to determine whether temperatures for one person 115 are consistent with temperatures for the other people detected in the environment). By performing clustering, the processing component 110 may handle temperature readings as relative readings to other temperature readings, rather than as exact measurements. That is, the processing component 110 may cluster temperatures and/or trackers based on a distance from the centroid of a cluster, where the distance may be based on a k-means distance function.

For example, when the system 100 detects a person 115 entering the view of the optical camera and the thermal sensor 105, the thermal sensor 105 may obtain one or more temperature readings for the person. The processing component 110 may add the person 115 to a cluster based on the temperature readings (e.g., a representative temperature 135 determined from the list of readings 140). For example, if the representative temperature 135 for a person 115 is within a threshold distance from the centroid of a cluster, the processing component 110 may assign the person 115 to that cluster. In some examples, the processing component 110 may apply one or more machine learning techniques to determine the threshold distance from the centroid of the cluster for assignment. The processing component 110 may establish a baseline for a cluster based on a relatively small cluster size (e.g., a cluster size of three trackers). As people enter the environment, a number of representative temperatures 135 for the people may normalize around one cluster, which the processing component 110 may set as the active cluster corresponding to the active baseline 145. The processing component 110 may maintain the clusters over a period of time if the system 100 detects people periodically or aperiodically over the period of time. For example, the processing component 110 may maintain a cluster throughout the day if at least one person 115 is added to the cluster every thirty minutes (or according to some other configured periodicity).

In some cases, the system 100 may track how a person 115 enters the environment. For example, if the environment corresponds to the entrance to a building, a person 115 entering the environment from outside the building may be subjected to a different ambient temperature than a person 115 entering the environment from inside the building. The system 100 may determine a direction of entry (e.g., using one or more neural networks) for a tracker and may maintain multiple active baselines 145 for different directions of entry. For example, the processing component 110 may manage a first active baseline 145 for people entering the view of the thermal sensor 105 from outdoors—and, correspondingly, from a first ambient temperature—and a second active baseline 145 for people entering the view of the thermal sensor 105 from indoors and a second ambient temperature. Additionally or alternatively, the system 100 may identify one or more people (e.g., a security guard) repeatedly entering the view of the thermal sensor 105 based on how the people enter the view, facial recognition techniques, or both. The system 100 may add such a person to a cluster the first time the person is detected and may refrain from adding the person to additional clusters or repeatedly adding the person to the same cluster based on identifying that the same person is being detected multiple times.

As illustrated in FIG. 1, person 115-a and person 115-b may enter a building from the outside. While a person 115 may typically have a body temperature between 97° F. and 99° F., where typical body temperatures approximately follow a normal distribution in this range, the person's skin temperature may fluctuate significantly based on the ambient temperature around the person 115. Additionally, a person 115 with a fever may have a body temperature above 99° F. (e.g., above 100.4° F.). Using an optical camera, the system 100 may detect the motion of each person 115 and determine that the motion corresponds to a person 115. For example, the optical camera, the processing component 110, or a combination thereof may determine a first set of pixels 120-a corresponding to the body of person 115-a and may detect the face of person 115-a within a second set of pixels 125-a. Similarly, the optical camera, the processing component 110, or a combination thereof may determine a first set of pixels 120-b corresponding to the body of person 115-b and may detect the face of person 115-b within a second set of pixels 125-b. The processing component 110 may assign each detected person 115 a unique tracker ID 130, such that person 115-a corresponds to tracker ID 130-a and person 115-b corresponds to tracker ID 130-b.

The thermal sensor 105 may obtain temperature readings for the face of each detected person 115. For example, as illustrated in FIG. 1, the thermal sensor 105 may manage two active trackers with tracker IDs 130-a and 130-b and may perform 9 temperature readings per second (e.g., based on a frame rate of the thermal sensor 105) for multiple areas of each face (e.g., around the eyes, below the nose, on the forehead, on the cheeks, or some combination thereof), such that the thermal sensor 105 obtains 18 temperature readings per measured area of the face per second. In some cases, the thermal sensor 105, the processing component 110, or both may reduce the storage overhead by aggregating multiple temperature readings into a single temperature reading for storage. For example, the thermal sensor 105 may obtain temperature readings for six areas of the face in a frame but may report a single temperature reading to the processing component 110 for the frame based on one or more of the six temperature readings. The processing component 110 may store, in memory with an association to tracker ID 130-a, a list of readings 140-a obtained for person 115-a. Based on the list of readings 140-a, the processing component 110 may determine a representative temperature 135-a for person 115-a. Similarly, the processing component 110 may store, in memory with an association to tracker ID 130-b, a list of readings 140-b obtained for person 115-b and a representative temperature 135-b for person 115-b.

The processing component 110 may cluster person 115-a and person 115-b based on the respective representative temperatures 135-a and 135-b. In some examples, person 115-a and person 115-b may be added to the same cluster (e.g., the cluster corresponding to the active baseline 145 or another cluster). In some other examples, person 115-a and person 115-b may be added to different clusters. Additionally, based on the representative temperatures 135-a and 135-b, the processing component 110 may determine whether person 115-a, person 115-b, or both have fevers according to a currently active baseline 145. If the processing component 110 determines that a person 115 (e.g., person 115-a) has a fever based on the active baseline 145, the processing component 110 may trigger an alert procedure. For example, the active baseline 145 may correspond to a cluster of temperatures currently identified as "typical," such that the centroid temperature of the cluster (e.g., a skin temperature reading) is assumed to correspond to a mean human body temperature. The active baseline 145 may support an offset value conversion from the centroid temperature of the cluster to the mean human body temperature. The processing component 110 may apply such an offset value to the representative temperature 135 for a person 115 to determine a corrected temperature for the person 115 (e.g., corresponding to the person's body temperature). The processing component 110 may trigger an alert procedure if the corrected temperature satisfies (e.g., exceeds) a temperature threshold (e.g., a fever threshold). Triggering the alert procedure may involve performing a checking process to confirm that the representative temperature 135 for the person 115 is not an error, sending an alert to a device or system, or both.

Figure 2:
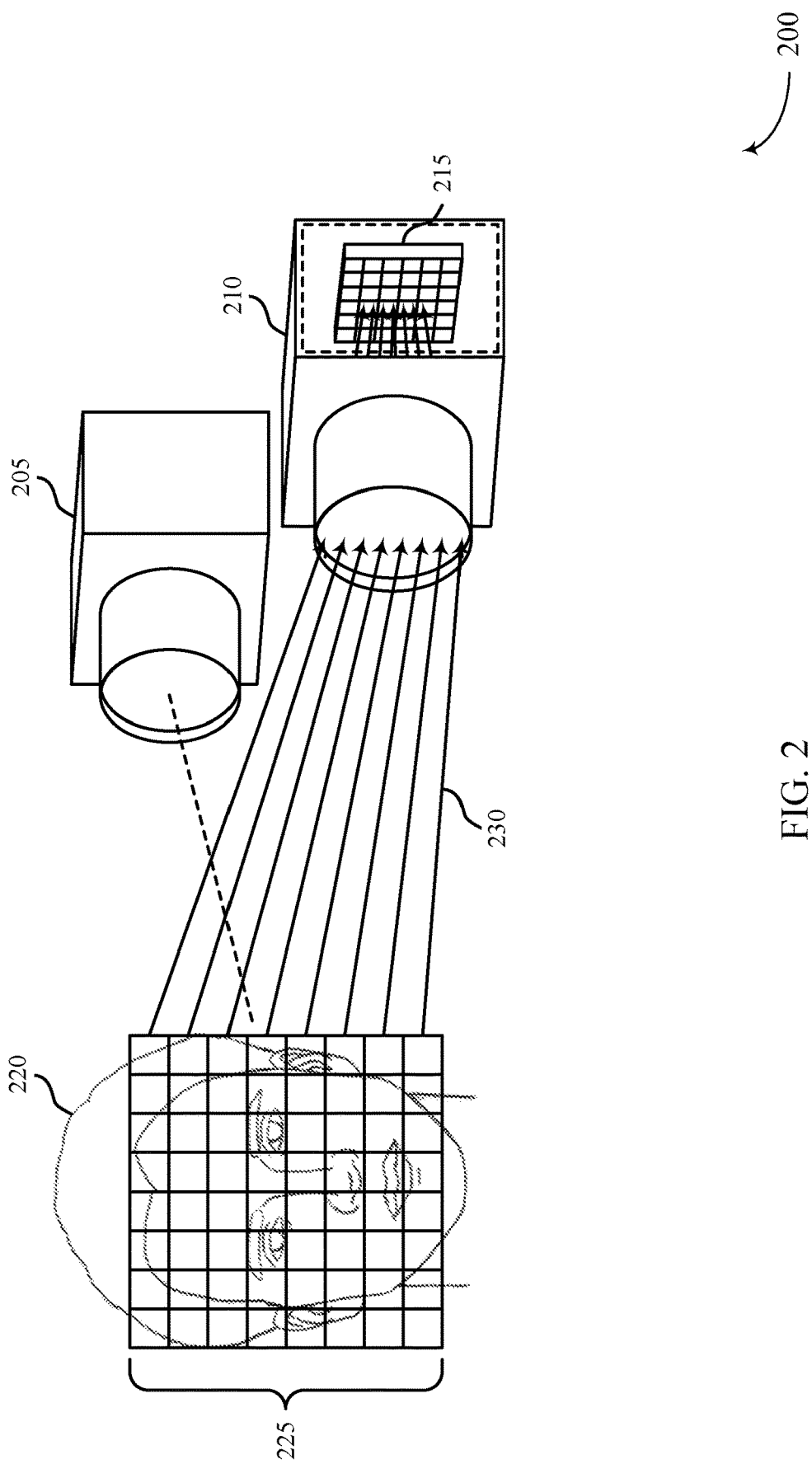
FIG. 2 illustrates an example of a temperature reading procedure that supports an AI procedure for normalizing thermal skin temperature to body temperature in accordance with aspects of the present disclosure.

FIG. 2 illustrates an example of a temperature reading procedure 200 that supports an AI procedure for normalizing thermal skin temperature to body temperature in accordance with aspects of the present disclosure. The temperature reading procedure 200 may support obtaining one or more temperature readings for a face 220 across one or more timestamps (e.g., for one or more frames). For example, an optical camera 205 may track a face 220 across multiple frames of a video. A thermal camera 210, including a thermal sensor, may obtain multiple temperature readings corresponding to multiple different portions of the face 220 for each frame. In some examples, the optical camera 205 and the thermal camera 210 may be jointly implemented at a single device. In some other examples, the optical camera 205 and the thermal camera 210 may communicate information via one or more connections, such that the thermal camera 210 may obtain temperature measurements based on the entities detected by the optical camera 205. The optical camera 205 and the thermal camera 210 may be aligned, such that the thermal camera 210—or a processing system supporting the thermal camera 210—may determine a conversion from one or more pixels of the optical camera 205 to one or more elements of the thermal camera 210.

The thermal camera 210 may implement a thermal sensor, such as a microbolometer 215. The microbolometer 215 may be an array of heat-detecting sensors that are sensitive to infrared radiation. When infrared energy strikes an individual bolometer element of the microbolometer 215, the element increases in temperature and the electrical resistance changes. The microbolometer 215 may measure the resistance change of the element to determine a corresponding temperature value.

The number of bolometer elements in the microbolometer 215 may determine the resolution of the microbolometer 215. For example, a high-resolution microbolometer 215 may include a large number of bolometer elements (e.g., thousands of elements) supporting detection of subtle temperature differences, even from objects positioned a significant distance from the thermal camera 210. However, a high-resolution microbolometer 215 may have fewer elements than a high-resolution optical camera 205 has pixels, such that there is not a one-to-one correlation between pixels and bolometer elements. For example, the microbolometer 215 may include a 384×260 array of bolometer elements to support precise temperature measurements, which may correspond to approximately a 1:4 bolometer element-to-pixel ratio. However, other microbolometer 215 resolutions and bolometer element-to-pixel ratios may be supported by the temperature reading procedure 200 described herein. The microbolometer 215 may support a high number of bolometer elements—and, correspondingly, a high-resolution—to support measuring thermal skin temperature of a face 220.

The microbolometer 215 may also support highly-precise temperature readings by the bolometer elements. For example, the microbolometer 215 may be able to distinguish between small differences in temperatures between the bolometer elements. This precision (e.g., the sensitivity of the bolometer elements) may be rated according to the noise equivalent temperature difference (NETD) rating of the microbolometer 215. The NETD rating may measure how well a thermal sensor is able to distinguish between very small differences in thermal radiation in an image. In some cases, the NETD rating may be referred to as the "thermal contrast" for a thermal sensor and may be measured in milli-Kelvin (mK). If the thermal noise in an image is equivalent to the smallest measurable temperature difference, the thermal sensor has reached the limit of its ability to resolve a useful thermal signal. The more noise there is, the higher the NETD value of the thermal sensor. A thermal sensor with a high NETD rating may support some operations (e.g., detecting leaks in a wall), but not others (e.g., accurately reading a person's skin temperature). The microbolometer 215 may support a low NETD rating—and, correspondingly, highly-sensitive detection capabilities—to support measuring thermal skin temperature of a face 220.

In some cases, a microbolometer 215 may be sensitive to temperature changes in a surrounding environment. For example, if the ambient temperature around the thermal camera 210 gets cooler, readings from the sensor elements may decrease. Similarly, if the ambient temperature around the thermal camera 210 gets warmer, readings from the sensor elements may increase. As such, the microbolometer 215 may effectively measure relative temperatures but may fail to measure absolute temperatures.

In some examples, a blackbody object may be used to calibrate the microbolometer 215 and mitigate the negative effects of ambient temperature on the accuracy of the microbolometer 215. A blackbody is an object which may absorb the radiation it receives—no matter the wavelength or direction—and may re-emit the absorbed radiation. The re-emitted energy level depends on the temperature of the blackbody and does not depend on other factors. As such, the blackbody may support calibration of a thermal sensor.

A "perfect" blackbody object may have an emissivity of 100% or 1.0. Other objects can be assigned an emissivity score relative to a perfect blackbody object. For example, polished copper may have an extremely low emissivity score of approximately 0.05. In contrast, a person (e.g., a face 220) may have an extremely high emissivity score of approximately 0.98.

A blackbody object may be used to calibrate a thermal sensor to account for ambient temperature changes in the environment around the sensor. For example, the calibration may mitigate the effects of ambient temperature on the thermal sensor. In some examples, the thermal camera 210 may be calibrated against a blackbody reference device prior to leaving a factory. Additionally or alternatively, the thermal camera 210 may repeatedly check the temperature of its external lens to automatically correct for changes to the ambient temperature around the thermal camera 210. In some examples, the thermal camera 210 may be calibrated or re-calibrated using any available blackbody reference device. In some other examples, an initial factory calibration may support accurate temperature readings without re-calibration. While the calibration may support mitigating the effects of changing ambient temperatures around the thermal sensor, the calibration may fail to mitigate the effects of other ambient temperatures on objects measured by the sensor. For example, if a person walks into an area and is measured by the thermal sensor without acclimating to the environment around the sensor, the blackbody device may not provide a calibration for accounting for an ambient temperature change on the skin temperature readings.

As an example, a thermal camera 210 may be set up inside a building lobby with a temperature of 72° F. Outside the building, the outdoor temperature may be 44° F. in the morning. Normal skin temperature for a person may vary slightly, but may typically be in a range from 92.3° F. to 98.4° F. A person walking to the building from their car may be on the lower end of (or below) this range based on the outdoor temperature of 44° F. For example, a person may enter the building with a skin temperature of 92° F. The thermal camera 210 may accurately measure the person's temperature of 92° F. (e.g., because the thermal camera 210 is calibrated to account for the 72° F. indoor temperature using a blackbody object as a reference during a manufacturing process or periodically while in production). In some cases, the outdoor temperature may warm up throughout the day. As other people enter the building throughout the day, they may show significantly higher temperatures than the person entering in the morning (e.g., based on the increased ambient outdoor temperature). As such, the temperature readings, while correct for each person's skin temperature, may vary significantly independent of the person's actual body temperature (e.g., and instead due to the ambient outdoor temperature). As such, the temperature readings may not appear consistent and may fail to accurately determine if a person has an elevated temperature. As such, calibrating the thermal camera 210 using a blackbody object may fail to support determining whether a person has an elevated body temperature (e.g., corresponding to a fever). Additionally, having a person wait for a period of time (e.g., 10 to 30 minutes) to acclimate to the indoor temperature may not be feasible in many environments, such as stores, transportation centers, etc.

As described with reference to the above example, the ambient temperature of a thermal camera 210 may be different from the ambient temperature of the object measured by the thermal camera 210 (e.g., a face 220). Additionally or alternatively, the ambient temperature around the thermal camera 210, the measured object, or both may dynamically change with the weather, the time of day, the time of year, or any combination thereof. For example, as described in the example above, the thermal camera 210 may determine a temperature of 92° F. for a person entering the building. To determine whether the person has a fever, the thermal camera 210—or a processing component supporting the thermal camera 210—may convert from the measured temperature to an actual body temperature. However, with just the single temperature reading of 92° F., the thermal camera 210 or processing component may not have enough information to determine a conversion, as the thermal camera 210 may not be able to determine how the outdoor ambient temperature affected the skin temperature of the person. In some cases, identifying the outdoor ambient temperature may not be sufficient to account for the effect of the outdoor ambient temperature on a person's skin temperature, as other factors may also affect the person's skin temperature (e.g., wind, previous ambient temperatures, or other factors).

Instead, the thermal camera 210 or corresponding processing component may use multiple temperature readings to determine a conversion from a measured skin temperature to an actual body temperature. To account for the dynamically changing ambient temperatures, the temperature reading procedure 200 may support real-time updates to one or more baselines. For example, using computer vision, machine learning, AI, or a combination thereof, the system supporting the optical camera 205 and the thermal camera 210 may automatically detect and correct for varying outside temperatures, for example, without operator intervention or calibration. The system may continuously learn, adapt, and respond to changes in ambient temperatures and other external factors (e.g., both affecting the thermal camera 210 and affecting any objects measured by the thermal camera 210) using one or more baselines.

For example, the system may use computer vision to detect and track individuals in the view of the optical camera 205. The system may identify the facial area of a detected person (e.g., as described with reference to FIG. 1) and may detect specific features of the face 220. The system may perform object detection to determine whether the person is wearing glasses, a mask, a hat, or other objects (e.g., using one or more detection algorithms). In some examples, the system may trigger an alert if the person is not wearing a mask (e.g., if a mask-mandate is in place). Based on the detection process, the system may determine portions of the face 220 to use for temperature readings. For example, the microbolometer 215 may use long-wave infrared 230, which may be inaccurate through glass. As such, if the system detects that the person is wearing glasses, the system may refrain from using the area around the eyes to obtain temperature readings (e.g., to improve the accuracy of the obtained temperature readings). The thermal camera 210 may perform a number of temperature detections per second for each detected face 220. In some cases, the system may store all of these temperature detections in memory for processing. In some other cases, the system may store a representative temperature reading based on the multiple temperature readings (e.g., a maximum temperature reading for a frame, a median temperature reading for the frame, a temperature reading from a specific area of the face for the frame, etc.). For example, for each face 220 in a frame, the thermal camera 210 may determine a single representative temperature value for the respective face 220. Based on repeatedly taking temperature readings as a person walks through the thermal camera's view, the system may obtain tens or hundreds of temperature readings for a single person. For example, the system may obtain up to ten temperature detections per second for a detected face 220.

Based on the detection by the optical camera 205, the system may identify one or more portions of the face 220 from which to detect temperature readings. In some examples, the system may prioritize specific portions of the face 220 based on predicted accuracy of the temperature readings. For example, the area around the eyes may be predicted to be most accurate, the area under the nose may be predicted to be the next most accurate, the forehead may be the next most accurate, the cheeks may be the next most accurate, and so on. If a portion of the face is covered (e.g., by glasses, a mask, an orientation of the face, etc.), the system may refrain from obtaining temperature readings from that portion of the face and instead may obtain temperature readings from other portions with skin visible.

As illustrated in FIG. 2, the optical camera 205 may detect a set of pixels 225 corresponding to a person's face 220. The thermal camera 210 may be aligned such that the thermal camera 210 may obtain temperature readings for the set of pixels 225 corresponding to the face 220 (e.g., using bolometer elements of the microbolometer 215). The number of pixels, bolometer elements, or both corresponding to the face 220 may be based on the resolution of the optical camera 205, the resolution of the thermal camera 210, the distance from one or both of the cameras to the face 220, or some combination thereof. For example, the system may perform temperature readings for a person when the person is a specific distance away from the optical camera 205, the thermal camera 210, or both. As an example, temperature readings may be obtained when the person is between six and sixteen feet away from the camera. The distance range for measuring temperature may support accurate temperature readings. As an example, within the distance range, the face may satisfy (e.g., exceed) a minimum number of pixels and/or bolometer elements and fail to satisfy (e.g., fail to exceed) a maximum number of pixels and/or bolometer elements. For example, the face 220 may correspond to a set of pixels 225 with a width of approximately 80 pixels, which may correspond to a set of bolometer elements with a width of approximately 20 bolometer elements. A width of 20 bolometer elements may support a sufficient resolution to obtain temperature readings for specific areas of the face 220. By taking temperature readings from very specific areas of the face 220, even if the face 220 is in motion, the system may support obtaining consistent and accurate skin temperature readings.

Using the obtained temperature readings, the system may compare a person's skin temperature to a recent history of other people's skin temperatures, for example, using a normalized baseline of skin temperatures. If the person's skin temperature fits within a calculated distance of an existing temperature baseline, the system may use the person's skin temperature to contribute to the existing baseline.

Accordingly, the system may automatically adjust the baseline to account for changes (e.g., even subtle changes) in ambient temperatures. The system may update the baseline in realtime or pseudo-realtime as people enter and exit the view of the optical camera 205 and the thermal camera 210, mitigating any latency involved in updating for changes to ambient temperatures. If a number of consistent temperature readings for a number of different faces 220 are added to a single baseline, the system may activate the baseline and use the active baseline to normalize temperature readings. If the system detects a face 220 and corresponding temperature reading when a baseline is active, the system may compare the temperature reading to the active baseline to determine if the corresponding person has a body temperature above a fever threshold.

If a person's skin temperature does not fit within a calculated distance of an active temperature baseline, the system may use the person's skin temperature to contribute to an inactive existing baseline or to create a new baseline. For example, the system may determine if the temperature reading for a face 220 corresponds to an existing baseline. If so, the system may determine the most relevant baseline (e.g., the baseline with a mean value closest to the temperature reading) and update the most relevant baseline with the temperature reading. If not, the system may create a new baseline starting with the temperature reading. If a number of temperature readings fall outside of a temperature range for the active baseline, the system may determine that the active baseline is unstable and may determine whether to deactivate the baseline, activate a different baseline, or both. Such a change in temperature readings may correspond to a long period of time passing between people walking into the view of the cameras or a significant change in temperature (e.g., either inside or outside) in a short period of time.

In this way, from a live video stream, the system may use AI techniques to detect people, detect faces 220, and track people and faces 220 over time. The system may support detecting multiple people concurrently and performing multiple concurrent temperature readings (e.g., using different bolometer elements of the microbolometer 215). Additionally or alternatively, using AI techniques, the system may manage a number of baselines to support adapting to different environments and changes within environments. The system may provide consistent, accurate body temperatures from a thermal camera 210 when the ambient temperature of the thermal camera 210 is different from an ambient temperature of the faces 220 measured by the thermal camera 210, when one or both of these ambient temperatures is changing, or both. Additionally, while a blackbody object may be used for additional calibration, the system may use AI techniques to handle relative temperatures without a blackbody calibration.

Figure 3:
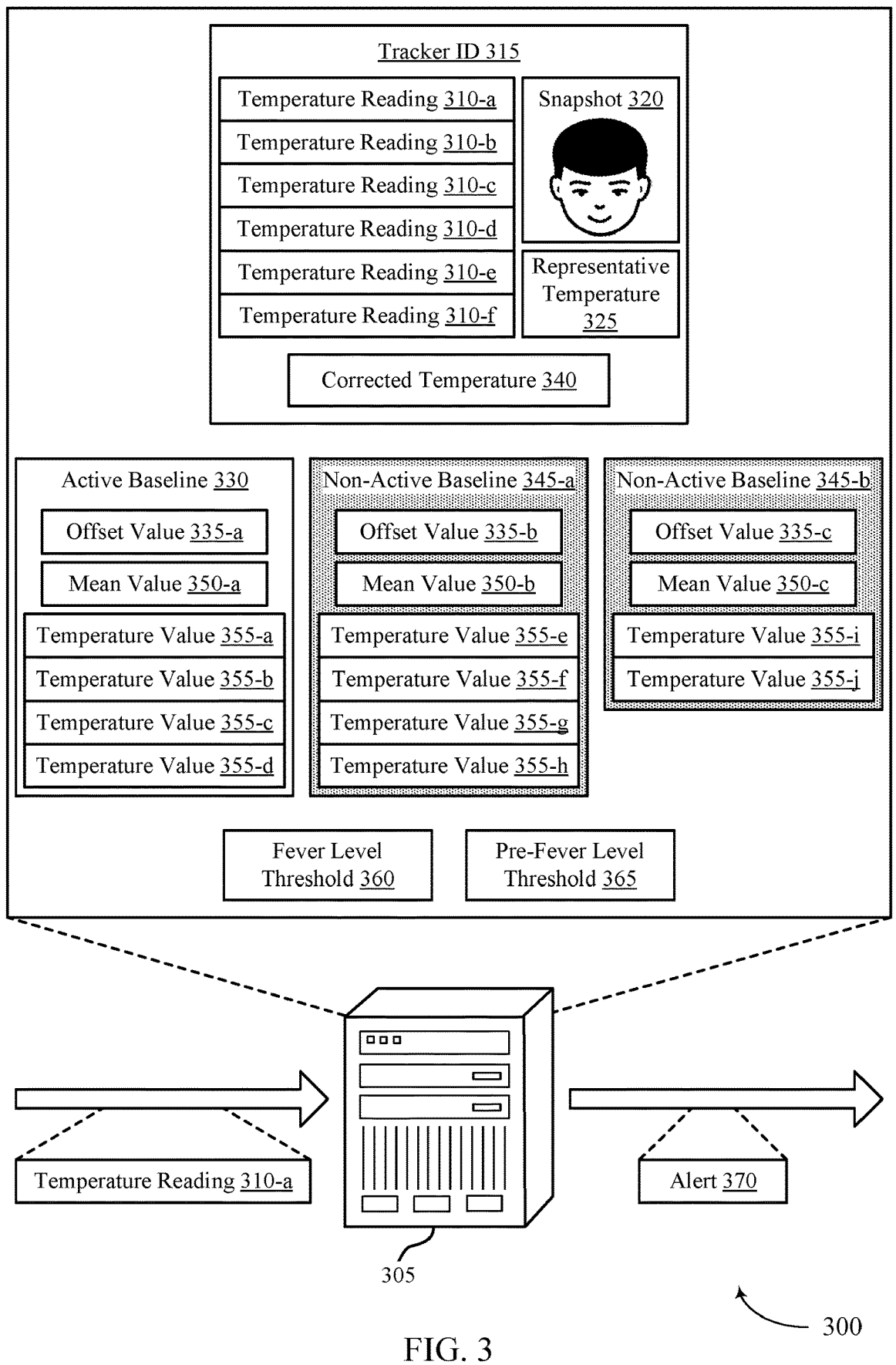
FIG. 3 illustrates an example of a tracker and baseline management system that supports an AI procedure for normalizing thermal skin temperature to body temperature in accordance with aspects of the present disclosure.

FIG. 3 illustrates an example of a tracker and baseline management system 300 that supports an AI procedure for normalizing thermal skin temperature to body temperature in accordance with aspects of the present disclosure. The tracker and baseline management system 300 may be implemented at a processing device 305, such as a server, a user device, or a processing component of a camera or sensor. For example, the processing device 305 may be an example of an optical camera component, a thermal camera component, a laptop, a desktop, a smart phone or other smart device, an application server, a database server, a cloud-based server, a server cluster, a virtual machine, a container, cloud computing resources, or any other device supporting memory storage, information processing, or both. The processing device 305 may leverage AI to track temperature readings 310 for a number of people, manage a set of baselines, and support alert procedures. For example, the processing device 305 may store, in memory, information related to multiple tracker IDs 315 corresponding to people detected by an optical camera, thermal camera, or both (e.g., as described with reference to FIG. 2).

The processing device 305 may receive a temperature reading 310-*a* from a thermal sensor. For example, the thermal sensor may send one or more temperature readings 310 for a detected face to the processing device 305 for processing and storage (e.g., as described with reference to FIG. 2). The temperature reading 310-*a* may be an example of an "uncorrected" temperature (e.g., may not be corrected based on a baseline to account for differences in ambient temperatures). As such, the temperature reading 310-*a* may be relative to an ambient temperature (e.g., an outdoor ambient temperature if the person is entering a building) and, correspondingly, may be relatively comparable to other such temperature readings 310, while not being comparable to temperature readings 310 associated with other ambient temperatures. The processing device 305 may implement an active baseline 330 to correct an "uncorrected" temperature reading. For example, using an offset value 335-*a* for the active baseline 330, the processing device 305 may calculate an absolute temperature from the temperature reading 310-*a* that supports comparison to a standard thermometer temperature for human fever detection.

The processing device 305 may receive the temperature reading 310-*a* with an association to a specific tracker (e.g., using a tracker ID 315). For example, the temperature reading 310-*a* may correspond to a specific timestamp (e.g., a specific frame of a video stream) and a specific face detected by an optical camera. The face may be linked to a specific tracker and corresponding tracker ID 315 (e.g., linking the face to a specific person in the view of the optical camera). The received temperature reading 310-*a* may be an example of a latest reading for a specific tracker. If no tracker ID 315 is currently assigned to the face, the processing device 305, the thermal sensor sending the temperature reading 310-*a*, or a combination thereof may assign a new tracker ID 315 to the face. In some cases, each tracker ID 315 may be associated in memory (or another storage medium) with information about the corresponding tracker. For example, the system may take and store a snapshot 320—or a series of snapshots 320—of the face to link the tracker to a specific face. Additionally or alternatively, the system may perform one or more identity recognition techniques to link the tracker to other aspects of a person (e.g., a name, contact information, or the like).

For a new temperature reading 310-*a* for a specific tracker ID 315, the processing device 305 may add the new temperature reading 310-*a* to a running list of temperature readings 310 for the tracker ID 315. The running list of temperature readings 310 may be stored in memory, a database, or some other storage system. The processing device 305 may remove an oldest temperature reading 310 from the list if the list exceeds a specific threshold length. For example, the processing device 305 may store the thirty most recent temperature readings 310 in memory for efficient access. Older temperature readings 310 may be moved to a database for storage and deleted from the memory of the processing device 305, or the older temperature readings 310 may be deleted from the memory of the processing device 305 without long-term storage in a database. In some examples, the processing device 305 may store multiple lists of temperature readings 310 for a tracker ID 315. For example, the processing device 305 may store a first list of descript temperature readings 310 (e.g., corresponding to a frontal face detected by the camera(s)) and a second list of mixed temperature readings 310, including descript readings and non-descript readings (e.g., corresponding to the side of a face or the back of a head detected by the camera(s)).

The processing device 305 may determine a representative temperature 325 for the tracker ID 315 based on the stored list of temperature readings 310. In some examples, the processing device 305 may remove one or more outlier readings in order to determine the representative temperature 325. The representative temperature 325 may be a maximum temperature, a mean temperature, a median temperature, or some other temperature reading.

In some cases, the processing device 305 may determine whether the hottest temperature reading 310 of the list of temperature readings 310 is within a threshold temperature range (e.g., 0.2° C.) from one or more next hottest temperature readings 310. For example, the processing device 305 may check the hottest reading against a number of next hottest readings corresponding to a value defined for a minimum number of readings for health logging and high-temperature alerts. The value may be a default value, a dynamically determined value, a value input by a user or administrative user, or any other value. For example, if the value is set to 3, the processing device 305 may determine whether the hottest temperature reading 310 is within the threshold temperature range—which similarly may be a default value, a dynamically determined value, a value input by a user or administrative user, or any other value—of the next 3 hottest temperature readings. If the hottest temperature reading 310 is within the threshold temperature range of the number of next hottest readings, the processing device 305 may set the hottest temperature reading 310 as the representative temperature 325. If not, the processing device 305 may check whether the second hottest temperature reading 310 is within the threshold temperature range of the number of next hottest readings after the second hottest temperature reading 310. If not, the processing device 305 may continue the checking process for the list until either a temperature reading 310 is determined to pass the check (e.g., indicating that the temperature reading 310 is not an outlier) or until reaching the end of the list. If the processing device 305 fails to identify a temperature reading 310 that passes the check, the processing device 305 may set the hottest temperature reading 310 as the representative temperature 325 but may indicate that this representative temperature 325 does not qualify for alerting (e.g., because the system may not have confidence in the accuracy of this reading). For example, the tracker ID 315 or representative temperature 325 may include a flag indicating whether or not the representative temperature 325 qualifies for alerting.

In some examples, the process for determining a representative temperature 325 may be performed on a list of descript temperature readings 310. In some other examples, the process may be performed on a list of mixed (e.g., descript and non-descript) temperature readings 310. Additionally or alternatively, if the process is performed on the list of descript temperature readings 310 and fails to identify a reading that qualifies for alerting, and if the list of mixed temperature readings 310 is different from the list of descript temperature readings 310, the processing device 305 may perform the process for determining a representative temperature 325 on the list of mixed temperature readings 310. As illustrated in FIG. 3, the processing device 305 may determine the representative temperature 325 based on a list of temperature readings including temperature reading 310-a (e.g., the latest temperature reading 310 received by the processing device 305), temperature reading 310-b, temperature reading 310-c, temperature reading 310-d, temperature reading 310-e, and temperature reading 310-f.

If the new temperature reading 310-a updates the representative temperature 325 associated with the tracker ID 315, the processing device 305 may update a baseline (e.g., the active baseline 330, a non-active baseline 345, or a new baseline) using the updated representative temperature 325. For example, the processing device 305 may check whether there is currently an active baseline 330. If so, the processing device 305 may determine whether the updated representative temperature 325 for the tracker ID 315 fits within the active baseline 330 (e.g., is within a threshold temperature difference from the mean value 350-a of the active baseline 330). If the updated representative temperature 325 is less than the threshold temperature difference (e.g., 0.55° C.) from the mean value 350-a of the active baseline 330, the processing device 305 may add the representative temperature 325 to the list of temperature values 355 contributing to the active baseline 330 (e.g., temperature value 355-a, temperature value 355-b, temperature value 355-c, and temperature value 355-d). As such, the tracker corresponding to the tracker ID 315 may contribute to the active baseline 330. The threshold temperature difference may be a default value (e.g., based on an expected temperature variance in human body temperatures), a dynamically determined value, a user input, or some combination thereof. In some examples, the processing device 305 may add the tracker or tracker ID to a cluster corresponding to the active baseline 330.

If the updated representative temperature 325 is greater than or equal to the threshold temperature difference from the mean value 350-a of the active baseline 330, the updated representative temperature 325 and corresponding tracker may be anomalous to the active baseline 330. If a threshold number of recently observed trackers are anomalous to the active baseline 330, the processing device 305 may deactivate the active baseline 330. The threshold number of trackers may be determined based on established baseline confidence loss conditions (e.g., default conditions, dynamically determined conditions, user input conditions, or a combination thereof). The threshold number of anomalous trackers may correspond to trackers most recently observed by the camera(s) or to trackers observed within a specific time window (e.g., within the last minute). Additionally or alternatively, the processing device 305 may deactivate an active baseline 330 if the processing device 305 has not received a temperature reading 310 for a detected face (e.g., a face that can contribute to a baseline) for a threshold time period (e.g., a few hours). The threshold time period may be a default time period, a dynamically determined time period, a user input time period (e.g., a health temperature baseline active time value), or a combination thereof.

For a tracker anomalous to the active baseline 330, the processing device 305 may determine whether the updated representative temperature 325 fits within a non-active baseline 345. For example, if the updated representative temperature 325 is less than a threshold temperature difference from the mean value 350 of a non-active baseline 345, the processing device 305 may add the representative temperature 325 to the list of temperature values 355 contributing to the non-active baseline 345. If the updated representative temperature 325 fits within multiple non-active baselines 345, the tracker may contribute to the non-active baseline 345 with the mean value 350 closest to the updated representative temperature 325. If the updated representative temperature 325 does not fit within the active baseline 330 or any non-active baseline 345, the processing device 305 may create a new non-active baseline 345 and may contribute to the new non-active baseline 345 with the tracker.

Contributing to a baseline may involve updating the temperature values for one or more baselines and re-calculating information related to the baseline (e.g., the mean value 350, the offset value 335, or both). For example, if the tracker corresponding to the tracker ID 315 contributed to a first baseline prior to updating the representative temperature 325, and the updated representative temperature 325 indicates that the tracker still contributes to the same baseline, the processing device 305 may overwrite the previous contribution with an updated contribution. For example, the processing device 305 may remove a temperature value 355 corresponding to the previous representative temperature 325 of the tracker and may add a temperature value 355 (e.g., temperature value 355-a) corresponding to the updated representative temperature 325 of the tracker to the list of temperature values 355 for the baseline. The processing device 305 may recalculate the offset value 335, the mean value 350, or both for the baseline based on the updated list of temperature values 355. The mean value 350 (e.g., mean value 350-a) may be calculated as the mean of the temperature values 355 for this baseline (e.g., the active baseline 330). The offset value 335 (e.g., offset value 335-a) may be calculated based on the mean value 350, the temperature values 355, or both for this baseline. For example, the offset value 335-a may be the difference between the mean human body temperature and the mean value 350-a for the active baseline 330. As such, the offset value 335-a may correspond to a conversion offset to convert from a representative temperature 325 (e.g., an uncorrected temperature corresponding to a representative skin temperature for a tracker) to a corrected temperature 340 (e.g., corresponding to a body temperature for the tracker). The offset value 335-a supports accounting for differences in ambient temperature around a thermal sensor (e.g., the sensor providing the temperature readings 310) and around an entity measured by the thermal sensor (e.g., a person's face). The offset value 335-a may be a positive offset value or a negative offset value.

If the updated representative temperature 325 indicates that the tracker contributes to a different baseline than the first baseline, the processing device 305 may remove a previous temperature value 355 corresponding to the previous representative temperature 325 of the tracker contributing to the first baseline and may add an updated temperature value 355 corresponding to the updated representative temperature 325 of the tracker to the list of temperature values 355 contributing to a second baseline. The processing device 305 may recalculate the offset value 335, the mean value 350, or both for both baselines based on removing the tracker's contribution to the first baseline and adding the tracker's contribution to the second baseline. In some cases, the processing device 305 may support a maximum number of trackers contributing to a baseline. If updating the contributions results in a baseline with a number of contributing trackers exceeding the maximum number of trackers (e.g., 12 trackers), the processing device 305 may remove a least recently added tracker's contribution to the baseline. The maximum number of trackers may be a default value, a dynamically determined value, a user input value, or a combination thereof.

In some cases, the processing device 305 may determine to merge one or more baselines based on the updated contributions. For example, if two baselines have mean values 350 that are within a threshold temperature difference from one another (e.g., 0.25° C.), the processing device 305 may merge the two baselines into a single, joint baseline. Merging the baselines may involve determining a joint list including the temperature values 355 from the merged baselines. If the joint list exceeds a maximum number of trackers that can contribute to a baseline, the processing device 305 may remove one or more tracker contributions from the merged list (e.g., the least recently added contributions for the merged list or one or more least recently added contributions from each individual list prior to merging). The processing device 305 may recalculate the mean value 350, the offset value 335, or both based on the merged list. As an example, the processing device 305 may determine to merge the active baseline 330 with the non-active baseline 345-b based on the mean value 350-a being within a threshold temperature difference from the mean value 350-c. The processing device 305 may merge the contributions for these two baselines, such that the merged baseline includes a list of contributed temperature values 355 including temperature value 355-a, temperature value 355-b, temperature value 355-c, temperature value 355-d, temperature value 355-i, and temperature value 355-j. The processing device 305 may recalculate a mean value 350 for the merged baseline based on the merged list of contributions (e.g., replacing the mean value 350-a and the mean value 350-c) and may recalculate an offset value 335 for the merged baseline based on the merged list of contributions (e.g., replacing the offset value 335-a and the offset value 335-c). In some cases, the merged baseline may remain as the active baseline 330 for the system.

In some cases, the processing device 305 may track whether each baseline stored in memory is a "solid" baseline. A "solid" baseline may correspond to a baseline that supports activation. In some examples, the processing device 305 may store a flag associated with each baseline, where the flag indicates whether or not the corresponding baseline is "solid." A baseline may be considered "solid" if, for a previous set of tracker contributions, at least a specific number (or percentage) of the contributions is towards the baseline. For example, a baseline may be marked as "solid" if, in the previous 7 different tracker contributions, at least 3 are towards the baseline. Other conditions for determining whether a baseline is "solid" may be supported by the processing device 305. In some examples, a user may define the conditions for determining whether a baseline is "solid."

The processing device 305 may determine whether to activate a baseline based on the updated contributions. For example, if the updated representative temperature 325 causes the tracker to contribute to a non-active baseline 345, the processing device 305 may determine whether to activate the updated non-active baseline 345. The processing device 305 may determine to activate the updated non-active baseline 345 if there is currently no active baseline (e.g., including if the processing device 305 deactivates the active baseline 330 based on one or more conditions) or if a number of most-recent contributions to the updated non-active baseline 345 (e.g., the last 3 contributions) are more recent than a most-recent contribution to the active baseline 330. The number of most-recent contributions to check to trigger activation may be a default value, a dynamically determined value, a user input value, or a combination thereof. Additionally or alternatively, the processing device 305 may check whether the updated non-active baseline 345 is a "solid" baseline. If the baseline is "solid" and meets the other conditions for activation, the processing device 305 may activate the updated non-active baseline 345. In some cases, the processing device 305 may check whether the updated non-active baseline 345 is "solid" if a user option (e.g., a strict baseline switching option, a strict baseline establishment option, or another user option) is turned on and may not check whether the updated non-active baseline 345 is "solid" if the user option is turned off.

As an example, the temperature reading 310-a may update the representative temperature 325 for the tracker ID 315. The updated representative temperature 325 may cause the tracker ID 315 to contribute to the non-active baseline 345-a based on the mean value 350-b for the non-active baseline 345-a. The processing device 305 may add the updated representative temperature 325 to the list of temperature values 355 (e.g., as temperature value 355-e) and may recalculate the offset value 335-b and the mean value 350-b for the non-active baseline 345-a based on the updated list of temperature values (e.g., including temperature value 355-e, temperature value 355-f, temperature value 355-g, and temperature value 355-h). The processing device 305 may determine that another baseline is currently active (e.g., the active baseline 330). However, the three most recent baseline contributions to the non-active baseline 345-a (e.g., corresponding to temperature value 355-e, temperature value 355-f, and temperature value 355-g) may be more recent than the most recent baseline contribution to the active baseline 330 (e.g., corresponding to temperature value 355-a). Additionally, the non-active baseline 345-a may either be a "solid" baseline or a user option for strict baseline switching may be turned off. Accordingly, the processing device 305 may deactivate the active baseline 330 and may activate the non-active baseline 345-a.

If there is an active baseline 330, the processing device 305 may use the active baseline 330 to determine a corrected temperature 340 for the tracker ID 315. The active baseline 330 may be a new active baseline (e.g., based on a baseline activation or deactivation procedure) or a maintained active baseline. The processing device 305 may calculate the corrected temperature 340 for the tracker ID 315 following updating the tracker's contribution to a baseline, a baseline activation procedure, or both. In some cases, the processing device 305 may refrain from calculating the corrected temperature 340 for the tracker ID 315 if the updated representative temperature 325 does not qualify for alerting. In some other cases, the processing device 305 may calculate the corrected temperature 340 for the tracker ID 315 but may refrain from triggering an alert procedure if the updated representative temperature 325 does not qualify for alerting.

The processing device 305 may calculate the corrected temperature 340 for the tracker ID 315 by adding the offset value 335-a for the active baseline 330 to the representative temperature 325 for the tracker ID 315. The offset value 335-a may be a positive value (e.g., if the mean value 350-a for the active baseline 330 is less than a mean human body temperature) or a negative value (e.g., if the mean value 350-a for the active baseline 330 is greater than the mean human body temperature). The mean human body temperature may be approximately 98° F. or 36.7° C. The temperatures and calculations managed and performed by the processing device 305 may be performed using measurements in K, F, or C.

The processing device 305 may compare the corrected temperature 340 for the tracker ID 315 to one or more temperature thresholds. For example, the processing device 305 may compare the corrected temperature 340 to a fever level threshold 360, a pre-fever level threshold 365, or both. In some cases, the fever level threshold 360 may be 38° C. or 100.4° F. and the pre-fever level threshold 365 may be 37.5° C. or 99.5° F. However, in some other cases, such thresholds may be set to different values (e.g., by a user) or dynamically determined.

If the corrected temperature 340 for the tracker ID 315 is above the fever level threshold 360, the processing device 305 may trigger an alert procedure. In some examples, the processing device 305 may implement a checking procedure for the tracker ID 315. The checking procedure may confirm whether the corrected temperature 340 exceeding the fever level threshold 360 is a legitimate fever-detection result. The processing device 305 may perform the checking procedure for a threshold time duration (e.g., a few seconds). The threshold time duration may be a default value, a dynamically determined value, a user input value (e.g., a high temperature delay set by a user), or a combination thereof. During the threshold time duration, the processing device 305 may set the corrected temperature 340 to a temporary value (e.g., a placeholder value that does not trigger sending an alert 370, such as 37.499° C. or 99.4982° F.).

During the threshold time duration, the thermal sensor may perform repeated measurements for the person corresponding to the tracker ID 315. Such measurements may be according to a standard measurement periodicity for the thermal sensor, or the processing device 305 may trigger the thermal sensor to perform additional measurements on the person's face during the threshold time duration based on the checking procedure. If, based on the additional temperature readings 310 during the checking procedure, the corrected temperature 340 for the tracker ID 315 falls and remains below the fever level threshold 360, the processing device 305 may refrain from sending an alert 370 (e.g., based on determining, during the checking procedure, that the corrected temperature 340 exceeding the fever level threshold 360 was a false fever detection). Additionally or alternatively, if, based on the additional temperature readings 310 during the checking procedure, the processing device 305 determines a corrected temperature 340 for the tracker ID 315 that is greater than an anomalous threshold (e.g., a default value, a dynamically determined value, a user input value, or a combination thereof, such as negative 0.2222° C.) away from the corrected temperature 340 that exceeded the fever level threshold 360, the fever level threshold 360, or both, the processing device 305 may determine that the corrected temperature 340 that exceeded the fever level threshold 360 is "improbable." Accordingly, the processing device 305 may report (e.g., store for the tracker ID 315) the temporary value (e.g., a value that does not trigger an alert 370, such as 37.499° C. or 99.4982° F.) as the corrected temperature 340 for the tracker ID 315. However, if, based on the additional temperature readings 310 during the checking procedure, the processing device 305 determines the corrected temperature 340 for the tracker ID 315 exceeds the fever level threshold 360, the processing device 305 may trigger an alert 370. In some other examples, the processing device 305 may not implement a checking procedure and instead may trigger the alert 370 based on the corrected temperature 340 for the tracker ID 315 first exceeding the fever level threshold 360.

Triggering an alert 370 may involve the processing device 305 sending an alert 370, for example, to another system or device. For example, the alert 370 may be an example of a digital indicator, a short message service (SMS) text message, an email message, or any other notification. In some examples, the processing device 305 may send the alert 370 to a user device associated with the person corresponding to the tracker ID 315 (e.g., if the processing device 305 determines the identity of the person based on one or more recognition techniques). In some other examples, the processing device 305 may send the alert 370 to a user device associated with a security entity, an administrative user, or another user. Additionally or alternatively, the alert 370 may be a visual, audio, or tactile component presented in a user interface. For example, the alert 370 may indicate a fever detection on a screen (e.g., to a security guard, to the person with the detected fever, or both). The alert 370 may include the determined corrected temperature 340, the representative temperature 325, the tracker ID 315, the snapshot 320 of the person's face, a name, username, or other identifier for the person, an indication of the active baseline 330 used to determine the corrected temperature 340, or any combination thereof. Additionally or alternatively, the processing device 305 or a database may store the information associated with the tracker ID 315, the baselines, or both (e.g., in a log), such that a user may review the information to determine how the measurements were determined.

In some cases, the processing device 305 may support multiple thresholds. For example, the processing device 305 may store a pre-fever level threshold 365. If the corrected temperature 340 for the tracker ID 315 exceeds the pre-fever level threshold 365, but not the fever level threshold 360, the processing device 305 may trigger an alert 370 indicating a pre-fever temperature. In some cases, the processing device 305 may implement a similar checking procedure to delay reporting a pre-fever temperature as described herein with respect to a detected fever temperature.

In some cases, the processing device 305 may retroactively trigger an alert 370. For example, new temperature readings 310 may update an active baseline 330, such that the mean value 350-*a*, the offset value 335-*a*, or both for the active baseline 330 are updated. Based on the updated offset value 335-*a*, the processing device 305 may determine that a corrected temperature 340 previously calculated for a tracker ID 315 exceeds the fever level threshold 360. To account for changes in ambient temperature, the processing device 305 may check recently determined corrected temperatures 340 for tracker IDs 315 (e.g., determined within a recent time period, such as the past 15 minutes), and may refrain from checking corrected temperatures 340 determined prior to this recent time period. In some cases, the processing device 305 may trigger an alert procedure for one or more tracker IDs 315 according to such a retroactive process.

Figure 4:
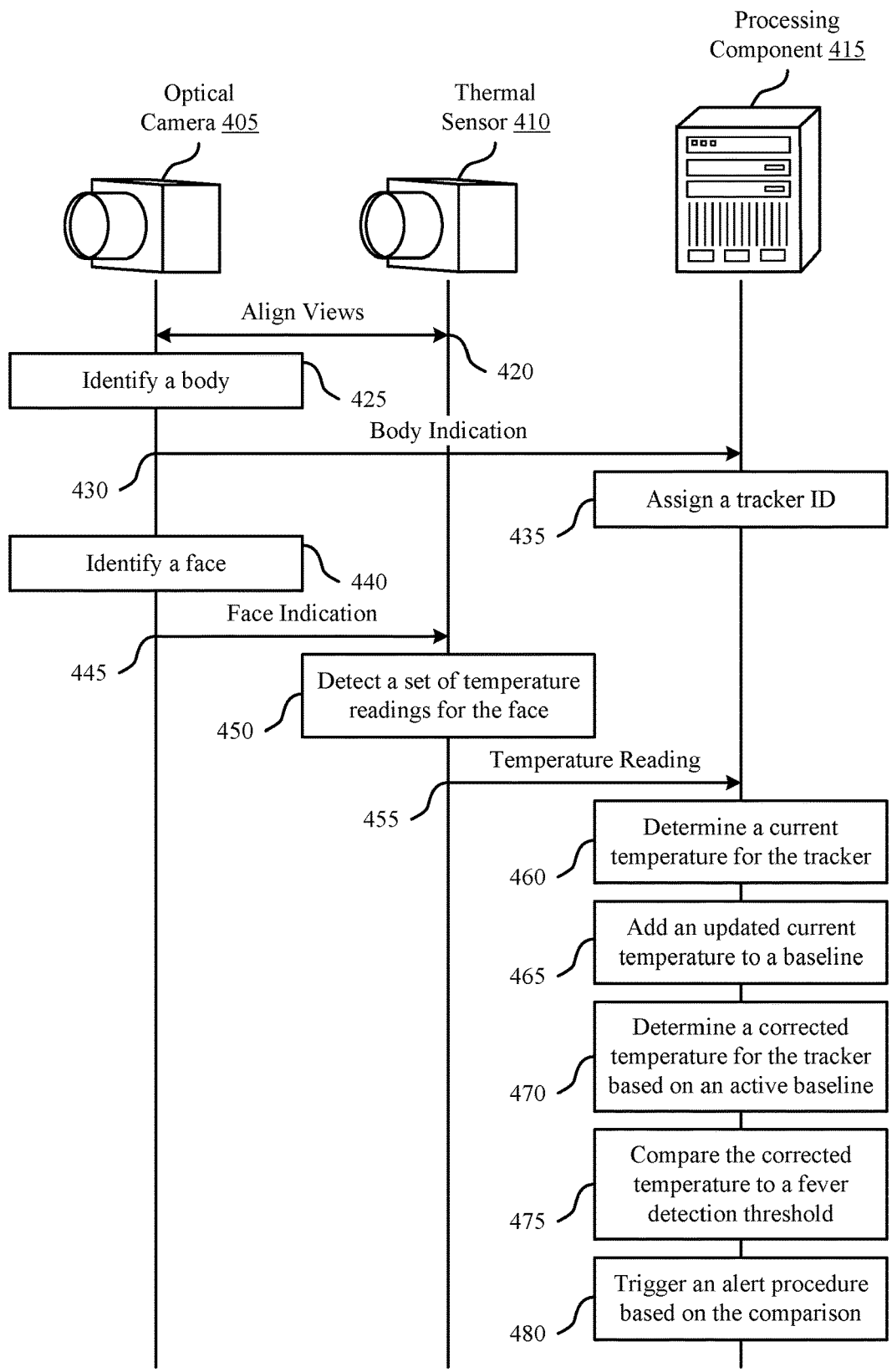
FIG. 4 illustrates an example of a process flow that supports an AI procedure for normalizing thermal skin temperature to body temperature in accordance with aspects of the present disclosure.

FIG. 4 illustrates an example of a process flow 400 that supports an AI procedure for normalizing thermal skin temperature to body temperature in accordance with aspects of the present disclosure. The process flow 400 may include an optical camera 405, a thermal sensor 410, and a processing component 415. These devices may be examples of the corresponding devices described with reference to FIGS. 1 through 3. In some examples, the processing component 415 may be a component of the optical camera 405, the thermal sensor 410, or both or may be a separate device (e.g., a server, a user device, cloud-computing resources, or another processing device or system). The optical camera 405, thermal sensor 410, and processing component 415 may operate together in a system to support detecting a person, obtaining temperature readings (e.g., thermal skin temperature readings) for the person, and implementing AI techniques to normalize the thermal skin temperature to a body temperature to support fever detection. Alternative examples of the following may be implemented, where some steps are performed in a different order than described or are not performed at all. In some cases, steps may include additional features not mentioned below, or further steps may be added.

At 420, the views of the optical camera 405 and the thermal sensor 410 may be aligned. In some examples, the optical camera 405 and the thermal sensor 410 may be components integrated in a single camera, and the camera may provide or perform the alignment. In some other examples, the processing component 415 may determine an alignment between the optical camera 405 and the thermal sensor 410. The alignment may support converting from a set of optical pixels at the optical camera 405 to a set of thermal pixels (e.g., corresponding to bolometer elements in a microbolometer) at the thermal sensor 410. In this way, the thermal sensor 410 may obtain temperature readings for specific features detected in an image by the optical camera 405.

At 425, the optical camera 405 may identify a body. For example, if the optical camera 405 is set up to capture video of an entrance to a building, the optical camera 405 may identify a person's body as the person enters the building. In some cases, the optical camera 405 may detect the body based on a motion detection procedure and a first neural network (e.g., to determine whether the detected motion corresponds to a person). At 430, the processing component 415 may receive an indication of the detected body. At 435, the processing component 415 may assign, in memory, a tracker ID to the body.

At 440, the optical camera 405 may identify a face on the body. In some cases, the optical camera 405 may determine a set of pixels corresponding to the body and may search a specific subset of the pixels (e.g., an upper third of the set of pixels) for a face. By first detecting the body before searching for the face, the optical camera 405, processing component 415, or both may reduce processing resources used for facial detection algorithms (e.g., a second neural network to detect a face) by reducing the area in which to search for the face. In some examples, the processing component 415 may further receive, from the optical camera 405, one or more images of the person's face and may store, in the memory, the one or more images of the person's face with a reference to the tracker ID.

At 445, the thermal sensor 410 may receive an indication of the detected face. The optical camera 405 may identify a first set of pixels corresponding to the face at the optical camera 405, and the thermal sensor 410 may identify a second set of pixels corresponding to the face at the thermal sensor 410 based on the alignment between the optical camera 405 and the thermal sensor 410.

At 450, the thermal sensor 410 may detect a set of temperature readings for the detected face. For example, the thermal sensor 410 may obtain the set of temperature readings from the second set of pixels corresponding to the face at the thermal sensor 410 in a frame. In some examples, the thermal sensor 410, the optical camera 405, the processing component 415, or a combination thereof may determine a distance from the face to the thermal sensor 410 and may adjust the set of temperature readings based on the determined distance. In some cases, the thermal sensor 410 may detect temperature readings from specific parts of the face (e.g., to support accurate temperature readings). For example, the thermal sensor 410 may prioritize obtaining temperature readings around the eyes or under the nose based on a predicted accuracy of such temperature readings. The thermal sensor 410 may identify, from the second set of pixels corresponding to the face, one or more first pixels associated with an optical region of the face (e.g., around the eyes), one or more second pixels associated with a nasal region of the face (e.g., under the nose), one or more third pixels associated with a forehead region of the face, or a combination thereof, where the set of temperature readings is detected from the one or more first pixels, the one or more second pixels, the one or more third pixels, or a combination thereof. The set of temperature readings may correspond to thermal skin temperature readings (e.g., uncorrected readings) for the face.

At 455, the thermal sensor 410 may send a temperature reading for the face to the processing component 415. For example, the thermal sensor 410 may send the set of temperature readings or may determine a representative temperature reading for the set of temperature readings and may send the representative temperature reading for the face to the processing component 415. In some cases, the temperature reading(s) may be associated with the tracker ID corresponding to the detected person. In this way, the processing component 415 may receive, from the thermal sensor 410, a temperature reading corresponding to a tracker ID such that the processing component 415 may effectively track temperature readings for multiple different people tracked by the system. The processing component 415 may add the temperature reading to a list in memory corresponding to the tracker ID and including previous temperature readings for the person. In some cases, the processing component 415 may remove, from the list in memory corresponding to the tracker ID, a least recently added temperature reading of the previous temperature readings based on the list in memory satisfying a threshold list length. For example, if the list supports a maximum list length of 30 temperature readings and adding the temperature reading causes the list to exceed the maximum list length, the processing component 415 may remove the oldest temperature reading from the list (such that the list corresponds to a rolling window of most recent temperature readings for a tracker).

At 460, the processing component 415 may determine a current temperature for the tracker ID based on the temperature reading and the previous temperature readings corresponding to the tracker ID (e.g., based on the list of temperature readings stored in memory for the tracker ID). In some cases, the processing component 415 may update the current temperature for the tracker ID based on the latest temperature reading from the thermal sensor 410. For example, to determine the current temperature for a tracker ID, the processing component 415 may iteratively determine whether a highest temperature reading of the list of temperature readings for the tracker ID corresponds to an outlier value. If the highest temperature reading is an outlier, the processing component 415 may remove this temperature reading as a candidate for the current temperature, and instead may determine whether the next highest temperature reading in the list is an outlier. The processing component 415 may set the current temperature for the tracker ID to the highest non-outlier temperature reading of the list based on the iterative process. In some examples, the current temperature may be a representative temperature for the tracker ID. In some cases, the processing component 415 may implement other techniques to determine a representative temperature for the tracker ID.

At 465, if the processing component 415 updates the current temperature for the tracker ID, the processing component 415 may add the updated current temperature to a baseline stored in memory. For example, the processing component 415 may add the updated current temperature to an active baseline, an inactive baseline, or a new baseline. Additionally, the processing component 415 may remove a previous current temperature for the tracker ID from a baseline (e.g., the active baseline or an inactive baseline) based on adding the updated current temperature for the tracker ID to a baseline. The processing component 415 may determine to which baseline to add the updated current temperature by comparing the updated current temperature to a mean value of the active baseline, one or more mean values of one or more inactive baselines, or a combination thereof.

At 470, the processing component 415 may determine a corrected temperature for the tracker ID based on the current temperature for the tracker ID. For example, the processing component 415 may add the updated current temperature to an offset value (e.g., an active baseline offset) for the active baseline to determine a corrected temperature for the tracker ID. The current temperature may be an example of a skin temperature for the person and the corrected temperature may be an example of a body temperature for the person.

At 475, the processing component 415 may compare the corrected temperature for the tracker ID to one or more temperature thresholds. For example, the processing component 415 may compare the corrected temperature to a fever detection threshold, a pre-fever detection threshold, or some combination of these or other thresholds. In some examples, a temperature threshold (e.g., the fever detection threshold) may be an example of an alert threshold for the active baseline. The processing component 415 may determine whether the updated current temperature for the tracker ID satisfied an alert threshold for the active baseline based on comparing the corrected temperature to the fever detection threshold.

At 480, the processing component 415 may trigger an alert procedure based on determining that the updated current temperature for the tracker ID satisfies the alert threshold. For example, the processing component 415 may trigger the alert procedure based on the corrected temperature exceeding the fever detection threshold based on the active baseline. In some cases, triggering the alert procedure may involve a checking procedure. For example, the processing component 415 may determine that the corrected temperature for the tracker ID exceeds the fever detection threshold, set the corrected temperature for the tracker ID to a temporary value below the fever detection threshold for a configured time duration, and receive, from the thermal sensor 410, multiple additional temperature readings corresponding to the tracker ID during the configured time duration. The processing component 415 may determine whether to execute an alert for the tracker ID based on the multiple additional temperature readings. If the processing component 415 determines to execute the alert—or if the processing component 415 does not implement the checking procedure—the processing component 415 may send an alert, for example, to a device, a system, a user interface, or some combination thereof. For example, the processing component 415 may transmit a digital indicator, an SMS message, an email message, or a combination thereof indicating the tracker ID, the corrected temperature for the tracker ID, or both based on determining to execute the alert.

Figure 5:
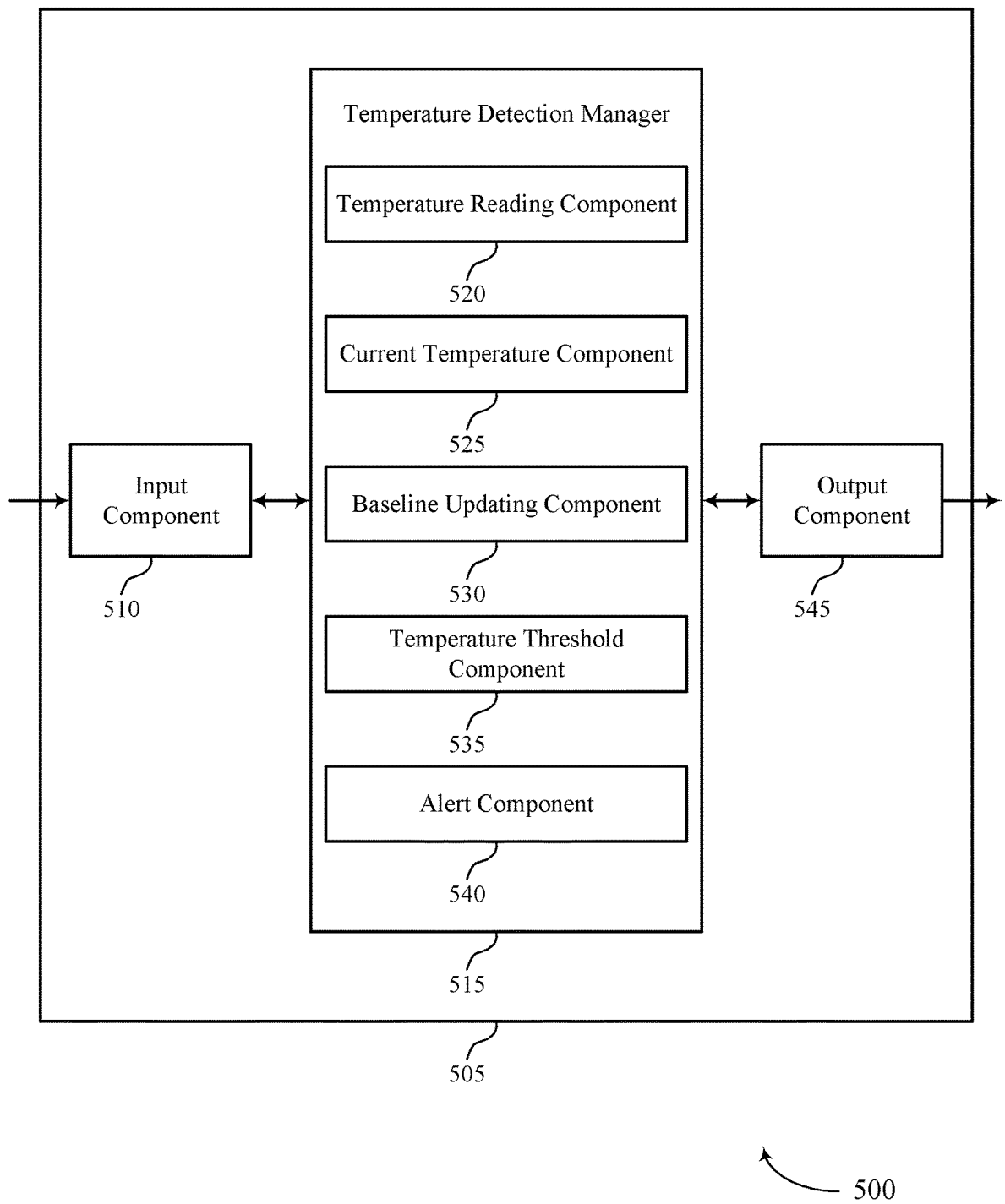
FIG. 5 shows a block diagram of an apparatus that supports an AI procedure for normalizing thermal skin temperature to body temperature in accordance with aspects of the present disclosure.

FIG. 5 shows a block diagram 500 of an apparatus 505 that supports an AI procedure for normalizing thermal skin temperature to body temperature in accordance with aspects of the present disclosure. The apparatus 505 may include an input component 510, a temperature detection manager 515, and an output component 545. The apparatus 505 may also include a processor. Each of these components may be in communication with one another (e.g., via one or more buses). In some cases, the apparatus 505 may be an example of a user device, a camera or other sensor, a server (e.g., application server, database server, cloud-based server, virtual machine, or other processing device), or a system containing multiple computing devices.

The input component 510 may manage input signals for the apparatus 505. For example, the input component 510 may identify input signals based on an interaction with a modem, a keyboard, a mouse, a touchscreen, or a similar device. Additionally or alternatively, the input signals may be examples of inputs to a sensor, such as an optical camera (e.g., an RGB camera), a thermal camera (e.g., using a microbolometer or another thermal sensor), or some combination thereof. These input signals may be associated with user input or processing at other components or devices. In some cases, the input component 510 may utilize an operating system such as iOS®, ANDROID®, MS-DOS®, MS-WINDOWS®, OS/2®, UNIX®, LINUX®, or another known operating system to handle input signals. The input component 510 may send aspects of these input signals to other components of the apparatus 505 for processing. For example, the input component 510 may transmit input signals to the temperature detection manager 515 to support normalizing thermal skin temperature to body temperature. In some cases, the input component 510 may be a component of an input/output (I/O) controller 715 as described with reference to FIG. 7.

The temperature detection manager 515 may include a temperature reading component 520, a current temperature component 525, a baseline updating component 530, a temperature threshold component 535, and an alert component 540. The temperature detection manager 515 may be an example of aspects of the temperature detection manager 605 or 710 described with reference to FIGS. 6 and 7.

The temperature detection manager 515 and/or at least some of its various sub-components may be implemented in hardware, software executed by a processor, firmware, or any combination thereof. If implemented in software executed by a processor, the functions of the temperature detection manager 515 and/or at least some of its various sub-components may be executed by a general-purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described in the present disclosure. The temperature detection manager 515 and/or at least some of its various sub-components may be physically located at various positions, including being distributed such that portions of functions are implemented at different physical locations by one or more physical devices. In some examples, the temperature detection manager 515 and/or at least some of its various sub-components may be a separate and distinct component in accordance with various aspects of the present disclosure. In other examples, the temperature detection manager 515 and/or at least some of its various sub-components may be combined with one or more other hardware components, including but not limited to an I/O component, a transceiver, a server, another computing device, one or more other components described in the present disclosure, or a combination thereof in accordance with various aspects of the present disclosure.

Means for performing the operations described herein with respect to the temperature detection manager 515 or various components of the temperature detection manager 515 may be performed by an optical camera, a thermal sensor, a processor integrated in the optical camera or the thermal sensor or otherwise connected to the optical camera, the thermal sensor, or both, or any combination of these or other devices (e.g., user devices, servers, sensors, etc.) supporting optical detection, thermal detection, data storage, data processing, or a combination thereof. The temperature reading component 520 may receive, from a thermal sensor, a temperature reading corresponding to a tracker ID. The current temperature component 525 may update a current temperature for the tracker ID based on the temperature reading and one or more previous temperature readings corresponding to the tracker ID stored in memory. The baseline updating component 530 may add the updated current temperature for the tracker ID to an active baseline, an inactive baseline, or a new baseline stored in the memory. The temperature threshold component 535 may determine that the updated current temperature for the tracker ID satisfies an alert threshold for the active baseline. The alert component 540 may trigger an alert procedure based on determining that the updated current temperature for the tracker ID satisfies the alert threshold.

The output component 545 may manage output signals for the apparatus 505. For example, the output component 545 may receive signals from other components of the apparatus 505, such as the temperature detection manager 515, and may transmit these signals to other components or devices. In some specific examples, the output component 545 may transmit output signals for display in a user interface, for storage in a database or data store, for further processing at a server or server cluster, or for any other processes at any number of devices or systems. In some cases, the output component 545 may be a component of an I/O controller 715 as described with reference to FIG. 7. The output component 545 may support any number of alerting procedures, such as sending a digital indicator, an SMS text message, an email, or any other type of notification indicating an alert.

Figure 6:
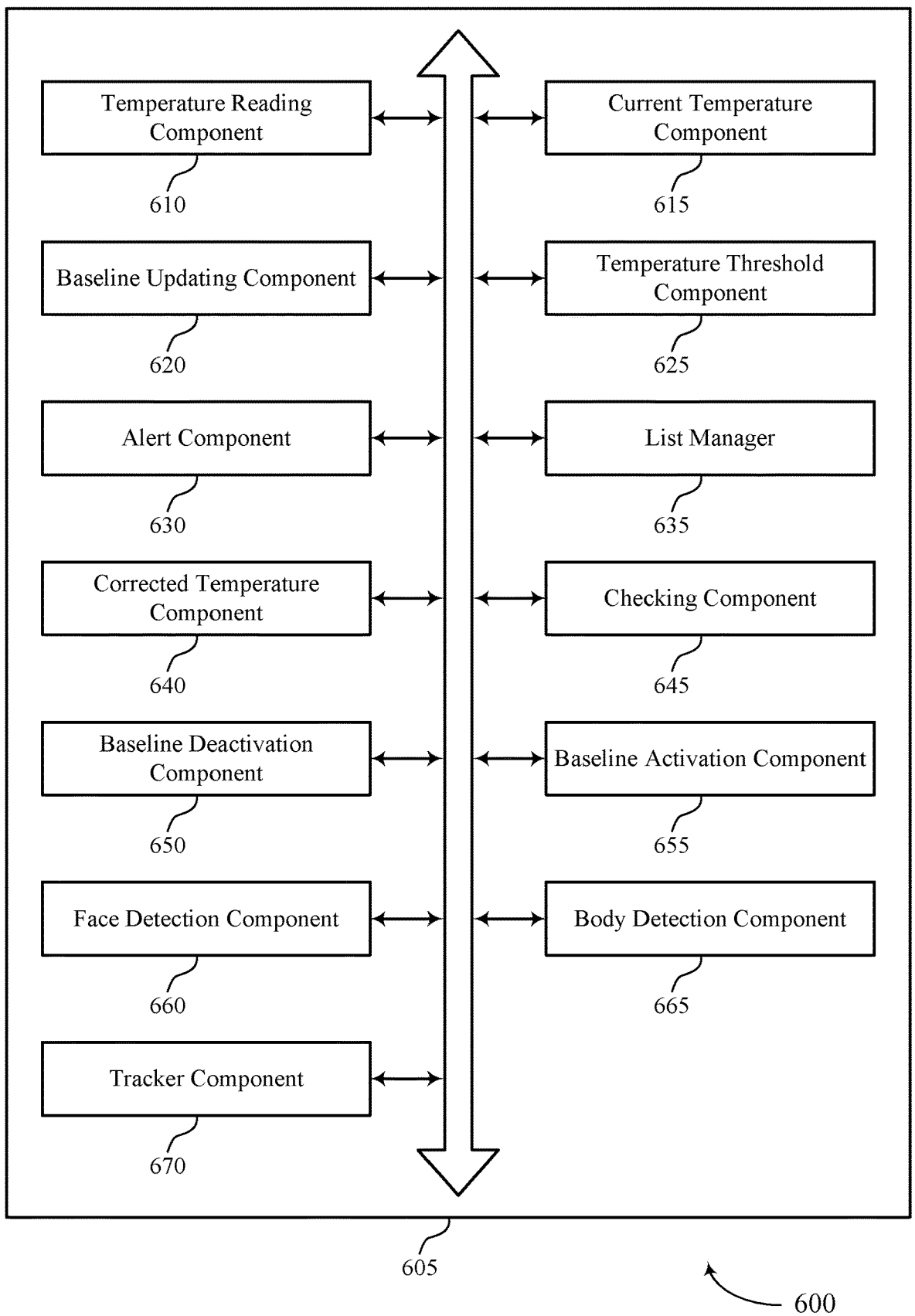
FIG. 6 shows a block diagram of a temperature detection manager that supports an AI procedure for normalizing thermal skin temperature to body temperature in accordance with aspects of the present disclosure.

FIG. 6 shows a block diagram 600 of a temperature detection manager 605 that supports an AI procedure for normalizing thermal skin temperature to body temperature in accordance with aspects of the present disclosure. The temperature detection manager 605 may be an example of aspects of a temperature detection manager 515 or a temperature detection manager 710 described herein. The temperature detection manager 605 may include a temperature reading component 610, a current temperature component 615, a baseline updating component 620, a temperature threshold component 625, an alert component 630, a list manager 635, a corrected temperature component 640, a checking component 645, a baseline deactivation component 650, a baseline activation component 655, a face detection component 660, a body detection component 665, a tracker component 670, or some combination thereof. One or more of these components may be implemented at or by an optical camera, a thermal sensor, a processor integrated in the optical camera or the thermal sensor or otherwise connected to the optical camera, the thermal sensor, or both, or any combination of these or other devices (e.g., user devices, servers, sensors, etc.) supporting optical detection, thermal detection, data storage, data processing, or a combination thereof. Each of these components may communicate, directly or indirectly, with one another (e.g., via one or more buses or other connections).

The temperature reading component 610 may receive, from a thermal sensor, a temperature reading corresponding to a tracker ID. The current temperature component 615 may update a current temperature for the tracker ID based on the temperature reading and one or more previous temperature readings corresponding to the tracker ID stored in memory. The baseline updating component 620 may add the updated current temperature for the tracker ID to an active baseline, an inactive baseline, or a new baseline stored in the memory. The temperature threshold component 625 may determine that the updated current temperature for the tracker ID satisfies an alert threshold for the active baseline. The alert component 630 may trigger an alert procedure based on determining that the updated current temperature for the tracker ID satisfies the alert threshold.

The list manager 635 may add the temperature reading to a list in the memory corresponding to the tracker ID and including the one or more previous temperature readings corresponding to the tracker ID. In some examples, the list manager 635 may remove, from the list in the memory corresponding to the tracker ID, a least recent temperature reading of the one or more previous temperature readings corresponding to the tracker ID based on the list in the memory satisfying a threshold list length.

In some examples, updating the current temperature for the tracker ID may involve the current temperature component 615 iteratively determining whether a highest temperature reading of the list in the memory corresponds to an outlier value and setting the current temperature for the tracker ID to a highest non-outlier temperature reading of the list in the memory based on the iterative determining.

In some examples, the baseline updating component 620 may remove a previous current temperature for the tracker ID from the active baseline, the inactive baseline, or the new baseline based on adding the updated current temperature for the tracker ID to the active baseline, the inactive baseline, or the new baseline.

In some examples, adding the updated current temperature for the tracker ID to the active baseline, the inactive baseline, or the new baseline may involve the baseline updating component 620 comparing the updated current temperature for the tracker ID to a mean value of the active baseline and one or more additional mean values of one or more inactive baselines stored in the memory and adding the updated current temperature for the tracker ID to the active baseline, the inactive baseline of the one or more inactive baselines, or the new baseline based on the comparing.

In some examples, triggering the alert procedure may involve the corrected temperature component 640 adding the updated current temperature for the tracker ID to an active baseline offset for the active baseline to determine a corrected temperature for the tracker ID. The updated current temperature may correspond to a skin temperature and the corrected temperature may correspond to a body temperature. The temperature threshold component 625 may compare the corrected temperature for the tracker ID to a fever detection threshold.

In some examples, the temperature threshold component 625 may determine that the corrected temperature for the tracker ID exceeds the fever detection threshold based on the comparing. In some such examples, the checking component 645 may set the corrected temperature for the tracker ID to a temporary value below the fever detection threshold for a configured time duration, receive, from the thermal sensor, a set of additional temperature readings corresponding to the tracker ID during the configured time duration, and determine whether to execute an alert for the tracker ID based on the set of additional temperature readings corresponding to the tracker ID.

In some examples, determining whether to execute the alert for the tracker ID may involve the checking component 645 determining to execute the alert for the tracker ID based on the set of additional temperature readings corresponding to the tracker ID, and the alert component 630 transmitting a digital indicator, an SMS message, an email message, or a combination thereof indicating the tracker ID, the corrected temperature for the tracker ID, or a combination thereof based on determining to execute the alert for the tracker ID.

In some examples, the baseline deactivation component 650 may compare the updated current temperature for the tracker ID to a mean value of the active baseline. In some examples, the baseline deactivation component 650 may determine that the updated current temperature for the tracker ID corresponds to an anomalous value for the active baseline based on the comparing. In some examples, the baseline deactivation component 650 may determine a number of anomalous values for the active baseline satisfies a threshold based on the updated current temperature for the tracker ID corresponding to the anomalous value and may deactivate the active baseline based on the number of anomalous values for the active baseline satisfying the threshold.

In some examples, the baseline deactivation component 650 may determine that a threshold time duration has passed since receiving a most recent temperature reading from the thermal sensor and may deactivate the active baseline based on the threshold time duration having passed since receiving the most recent temperature reading.

In some examples, the updated current temperature for the tracker ID may be added to a first inactive baseline of one or more inactive baselines stored in the memory. In some such examples, the baseline activation component 655 may determine that a threshold number of current temperatures have been added to the first inactive baseline more recently than a most recent current temperature has been added to the active baseline. The baseline deactivation component 650 may deactivate the active baseline based on the threshold number of current temperatures having been added to the first inactive baseline more recently than the most recent current temperature has been added to the active baseline, and the baseline activation component 655 may activate the first inactive baseline based on the threshold number of current temperatures having been added to the first inactive baseline more recently than the most recent current temperature has been added to the active baseline.

The face detection component 660 may identify, at an optical camera, a first set of pixels corresponding to a face. In some examples, the face detection component 660 may identify, at the thermal sensor, a second set of pixels corresponding to the face based on an alignment between the optical camera and the thermal sensor. In some examples, the temperature reading component 610 may detect, at the thermal sensor, a set of temperature readings from the second set of pixels for a frame, where the temperature reading corresponding to the tracker ID is received based on the set of temperature readings.

The body detection component 665 may detect, at the optical camera, a body based on a motion detection procedure and a first neural network, where the first set of pixels corresponding to the face is identified based on the detected body and a second neural network. The tracker component 670 may assign, in the memory, the tracker ID to the body.

In some examples, the active baseline may be an example of a first active baseline, and the body detection component 665 may determine that the tracker ID corresponds to the first active baseline of a set of active baselines based on a direction that the body entered a view of the optical camera.

In some examples, the body may be detected in a first frame of the optical camera, and the body detection component 665 may detect, at the optical camera, the body in a second frame of the optical camera. In some examples, the tracker component 670 may maintain, in the memory, the tracker ID assigned to the body based on detecting the body in the second frame.

In some examples, the face detection component 660 may receive, from the optical camera, an image of the face, and the tracker component 670 may store, in the memory, the image of the face and a reference to the tracker ID.

In some examples, the face detection component 660 may determine a distance from the face to the thermal sensor, and the temperature reading component 610 may adjust the set of temperature readings based on the determined distance.

In some examples, detecting the set of temperature readings from the second set of pixels for the frame may involve the temperature reading component 610 identifying, from the second set of pixels, one or more first pixels associated with an optical region of the face, one or more second pixels associated with a nasal region of the face, one or more third pixels associated with a forehead region of the face, or a combination thereof, where the set of temperature readings are detected from the one or more first pixels, the one or more second pixels, the one or more third pixels, or a combination thereof, and the set of temperature readings include thermal skin temperature readings for the face.

Figure 7:
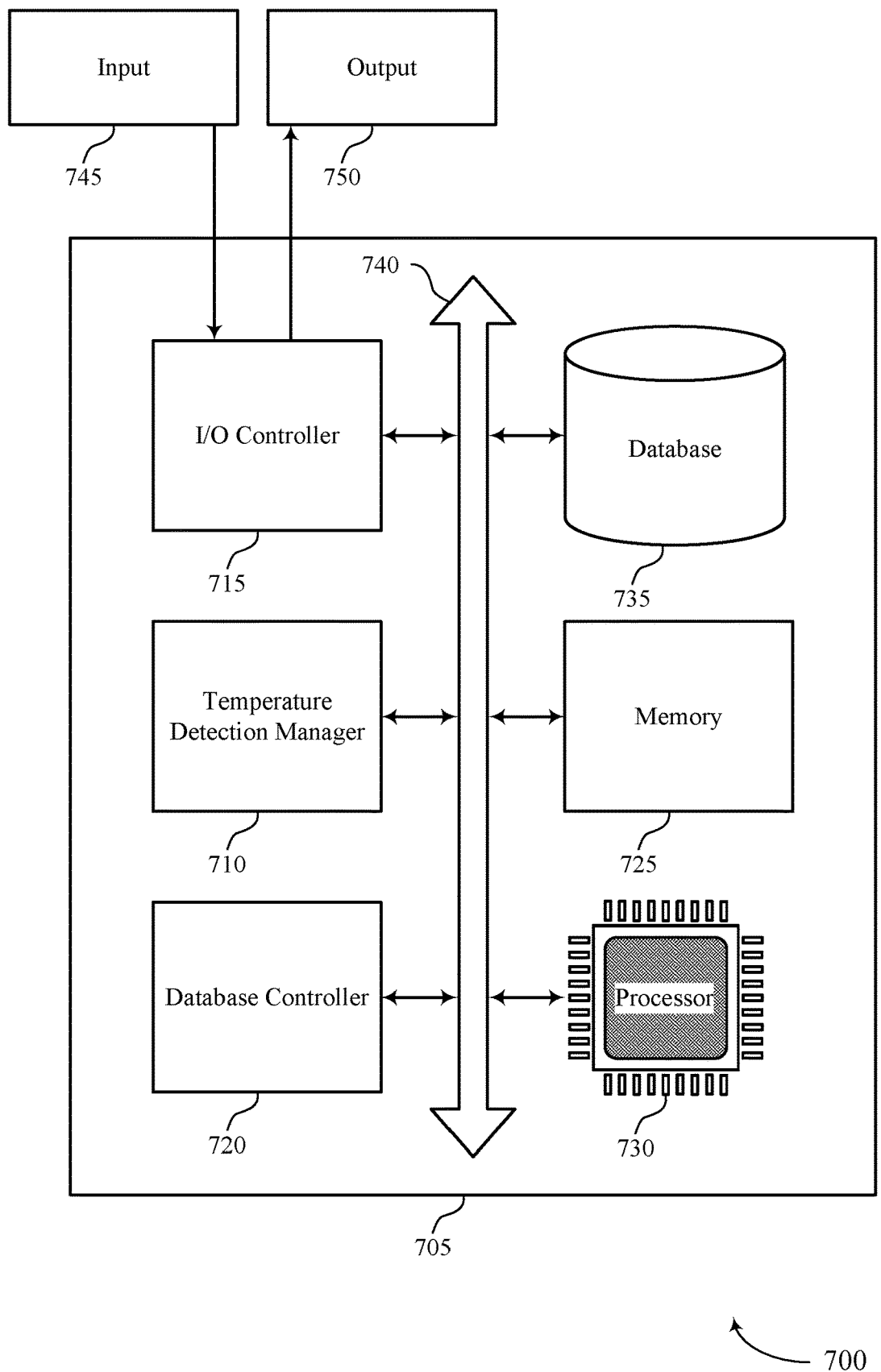
FIG. 7 shows a diagram of a system including a device that supports an AI procedure for normalizing thermal skin temperature to body temperature in accordance with aspects of the present disclosure.

FIG. 7 shows a diagram of a system 700 including a device 705 that supports an AI procedure for normalizing thermal skin temperature to body temperature in accordance with aspects of the present disclosure. The device 705 may be an example of or include the components of a camera, a sensor, a user device, a processing device (e.g., server, server cluster, virtual machine, etc.), an apparatus 505, or any combination thereof as described herein. The device 705 may include components for bi-directional data communications including components for transmitting and receiving communications, including a temperature detection manager 710, an I/O controller 715, a database controller 720, memory 725, a processor 730, a database 735, or some combination thereof. These components may be in electronic communication via one or more buses (e.g., bus 740) or other connections.

The temperature detection manager 710 may be an example of a temperature detection manager 515 or 605 as described herein. For example, the temperature detection manager 710 may perform any of the methods or processes described above with reference to FIGS. 5 and 6. In some cases, the temperature detection manager 710 may be implemented in hardware, software executed by a processor, firmware, or any combination thereof.

The I/O controller 715 may manage input signals 745 and output signals 750 for the device 705. The I/O controller 715 may also manage peripherals not integrated into the device 705. In some cases, the I/O controller 715 may represent a physical connection or port to an external peripheral. In some cases, the I/O controller 715 may utilize an operating system such as iOS®, ANDROID®, MS-DOS®, MS-WINDOWS®, OS/2®, UNIX®, LINUX®, or another known operating system. In other cases, the I/O controller 715 may represent or interact with a modem, a keyboard, a mouse, a touchscreen, or a similar device. In some cases, the I/O controller 715 may be implemented as part of a processor. In some cases, a user may interact with the device 705 via the I/O controller 715 or via hardware components controlled by the I/O controller 715.

The database controller 720 may manage data storage and processing in a database 735. In some cases, a user may interact with the database controller 720. In other cases, the database controller 720 may operate automatically without user interaction. The database 735 may be an example of a single database, a distributed database, multiple distributed databases, a data store, or an emergency backup database.

Memory 725 may include random-access memory (RAM) and read-only memory (ROM). The memory 725 may store computer-readable, computer-executable software including instructions that, when executed, cause the processor to perform various functions described herein. In some cases, the memory 725 may contain, among other things, a basic I/O system (BIOS) which may control basic hardware or software operation such as the interaction with peripheral components or devices.

The processor 730 may include an intelligent hardware device (e.g., a general-purpose processor, a DSP, a central processing unit (CPU), a microcontroller, an ASIC, an FPGA, a programmable logic device, a discrete gate or transistor logic component, a discrete hardware component, or any combination thereof). In some cases, the processor 730 may be configured to operate a memory array using a memory controller. In other cases, a memory controller may be integrated into the processor 730. The processor 730 may be configured to execute computer-readable instructions stored in a memory 725 to perform various functions (e.g., functions or tasks supporting an AI procedure for normalizing thermal skin temperature to body temperature).

Figure 8:
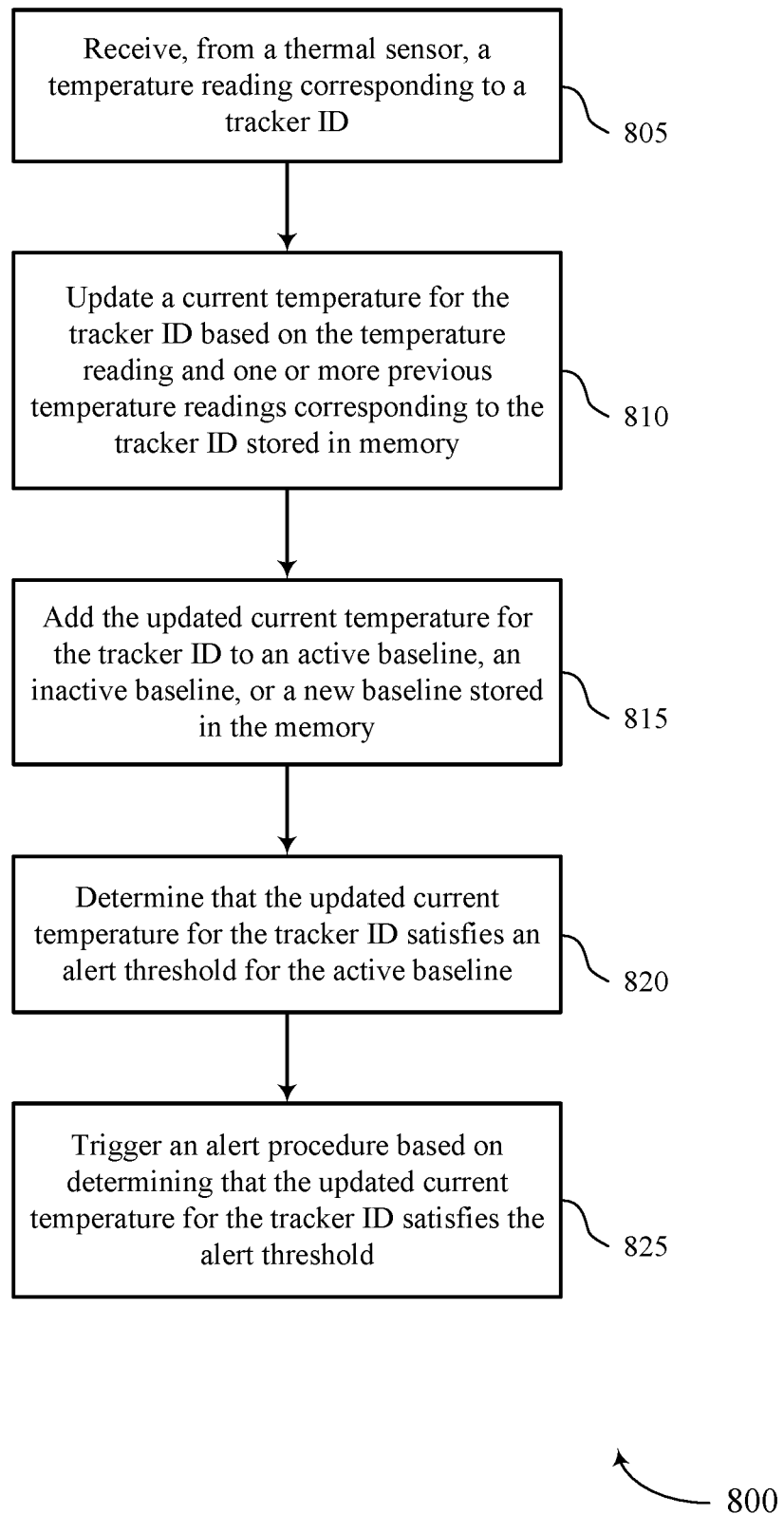
FIGS. 8 through 10 show flowcharts illustrating methods that support an AI procedure for normalizing thermal skin temperature to body temperature in accordance with aspects of the present disclosure.

FIG. 8 shows a flowchart illustrating a method 800 that supports an AI procedure for normalizing thermal skin temperature to body temperature in accordance with aspects of the present disclosure. The operations of method 800 may be implemented by a processing device or its components as described herein. For example, the operations of method 800 may be performed by a temperature detection manager as described with reference to FIGS. 5 through 7. The processing device may be an example of a camera, a sensor, a user device, a server (e.g., an application server, a database server, a cloud-based server, a worker server, a server cluster, a virtual machine, a container, or any combination of these or other devices or systems supporting data processing), or any combination thereof. In some examples, a processing device may execute a set of instructions to control the functional elements of the processing device to perform the functions described below. Additionally or alternatively, a processing device may perform aspects of the functions described below using special-purpose hardware.

At 805, the processing device may receive, from a thermal sensor, a temperature reading corresponding to a tracker ID. The operations of 805 may be performed according to the methods described herein. In some examples, aspects of the operations of 805 may be performed by a temperature reading component as described with reference to FIGS. 5 through 7.

At 810, the processing device may update a current temperature for the tracker ID based on the temperature reading and one or more previous temperature readings corresponding to the tracker ID stored in memory. The operations of 810 may be performed according to the methods described herein. In some examples, aspects of the operations of 810 may be performed by a current temperature component as described with reference to FIGS. 5 through 7.

At 815, the processing device may add the updated current temperature for the tracker ID to an active baseline, an inactive baseline, or a new baseline stored in the memory. The operations of 815 may be performed according to the methods described herein. In some examples, aspects of the operations of 815 may be performed by a baseline updating component as described with reference to FIGS. 5 through 7.

At 820, the processing device may determine that the updated current temperature for the tracker ID satisfies an alert threshold for the active baseline. The operations of 820 may be performed according to the methods described herein. In some examples, aspects of the operations of 820 may be performed by a temperature threshold component as described with reference to FIGS. 5 through 7.

At 825, the processing device may trigger an alert procedure based on determining that the updated current temperature for the tracker ID satisfies the alert threshold. The operations of 825 may be performed according to the methods described herein. In some examples, aspects of the operations of 825 may be performed by an alert component as described with reference to FIGS. 5 through 7.

Figure 9:
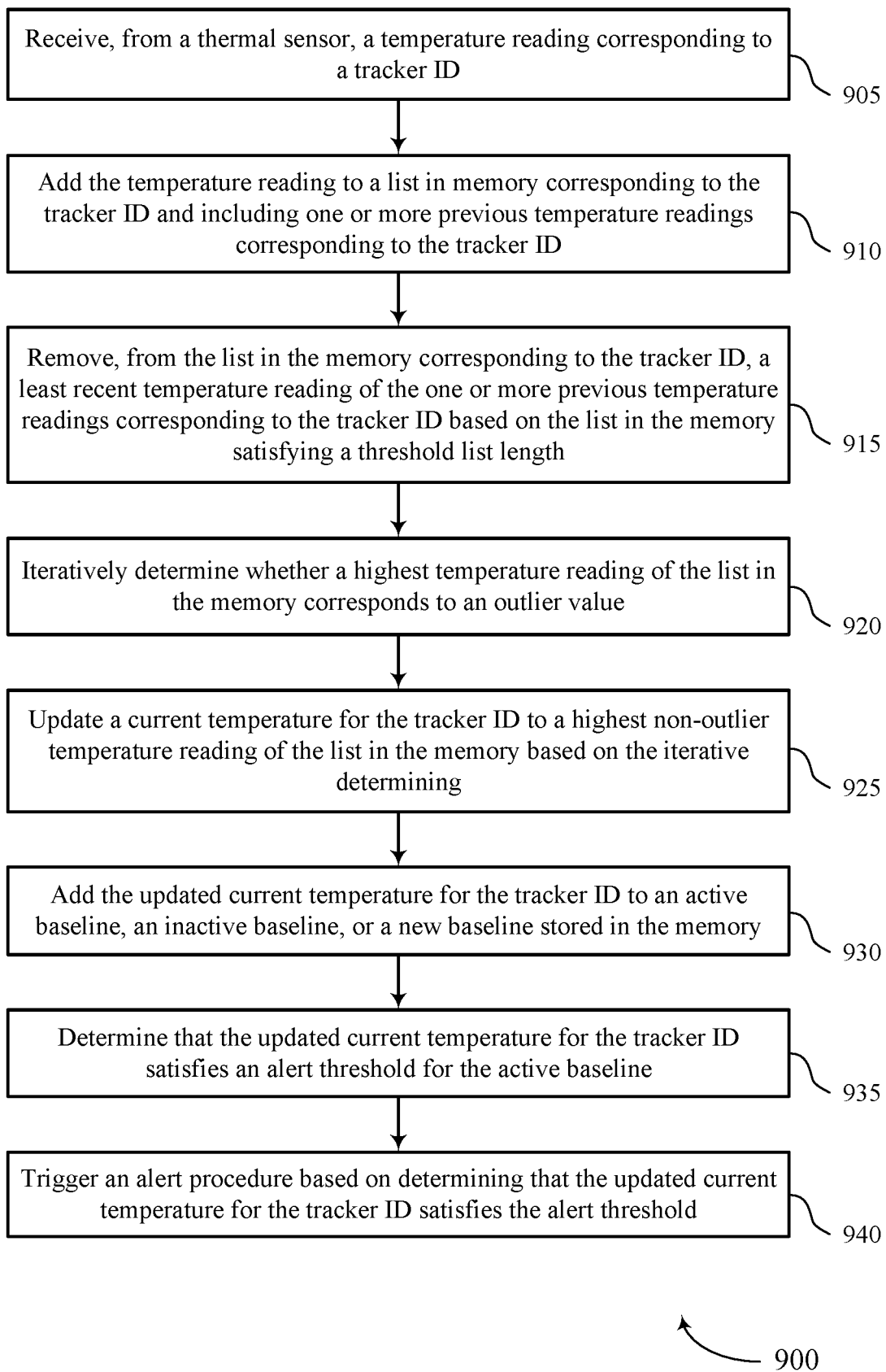

FIG. 9 shows a flowchart illustrating a method 900 that supports an AI procedure for normalizing thermal skin temperature to body temperature in accordance with aspects of the present disclosure. The operations of method 900 may be implemented by a processing device or its components as described herein. For example, the operations of method 900 may be performed by a temperature detection manager as described with reference to FIGS. 5 through 7. The processing device may be an example of a camera, a sensor, a user device, a server (e.g., an application server, a database server, a cloud-based server, a worker server, a server cluster, a virtual machine, a container, or any combination of these or other devices or systems supporting data processing), or any combination thereof. In some examples, a processing device may execute a set of instructions to control the functional elements of the processing device to perform the functions described below. Additionally or alternatively, a processing device may perform aspects of the functions described below using special-purpose hardware.

At 905, the processing device may receive, from a thermal sensor, a temperature reading corresponding to a tracker ID. The operations of 905 may be performed according to the methods described herein. In some examples, aspects of the operations of 905 may be performed by a temperature reading component as described with reference to FIGS. 5 through 7.

At 910, the processing device may add the temperature reading to a list in memory corresponding to the tracker ID and including one or more previous temperature readings corresponding to the tracker ID. The operations of 910 may be performed according to the methods described herein. In some examples, aspects of the operations of 910 may be performed by a list manager as described with reference to FIGS. 5 through 7.

At 915, the processing device may remove, from the list in the memory corresponding to the tracker ID, a least recent temperature reading of the one or more previous temperature readings corresponding to the tracker ID based on the list in the memory satisfying a threshold list length. The operations of 915 may be performed according to the methods described herein. In some examples, aspects of the operations of 915 may be performed by a list manager as described with reference to FIGS. 5 through 7.

At 920, the processing device may iteratively determine whether a highest temperature reading of the list in the memory corresponds to an outlier value. The operations of 920 may be performed according to the methods described herein. In some examples, aspects of the operations of 920 may be performed by a current temperature component as described with reference to FIGS. 5 through 7.

At 925, the processing device may update a current temperature for the tracker ID to a highest non-outlier temperature reading of the list in the memory based on the iterative determining. The operations of 925 may be performed according to the methods described herein. In some examples, aspects of the operations of 925 may be performed by a current temperature component as described with reference to FIGS. 5 through 7.

At 930, the processing device may add the updated current temperature for the tracker ID to an active baseline, an inactive baseline, or a new baseline stored in the memory. The operations of 930 may be performed according to the methods described herein. In some examples, aspects of the operations of 930 may be performed by a baseline updating component as described with reference to FIGS. 5 through 7.

At 935, the processing device may determine that the updated current temperature for the tracker ID satisfies an alert threshold for the active baseline. The operations of 935 may be performed according to the methods described herein. In some examples, aspects of the operations of 935 may be performed by a temperature threshold component as described with reference to FIGS. 5 through 7.

At 940, the processing device may trigger an alert procedure based on determining that the updated current temperature for the tracker ID satisfies the alert threshold. The operations of 940 may be performed according to the methods described herein. In some examples, aspects of the operations of 940 may be performed by an alert component as described with reference to FIGS. 5 through 7.

Figure 10:
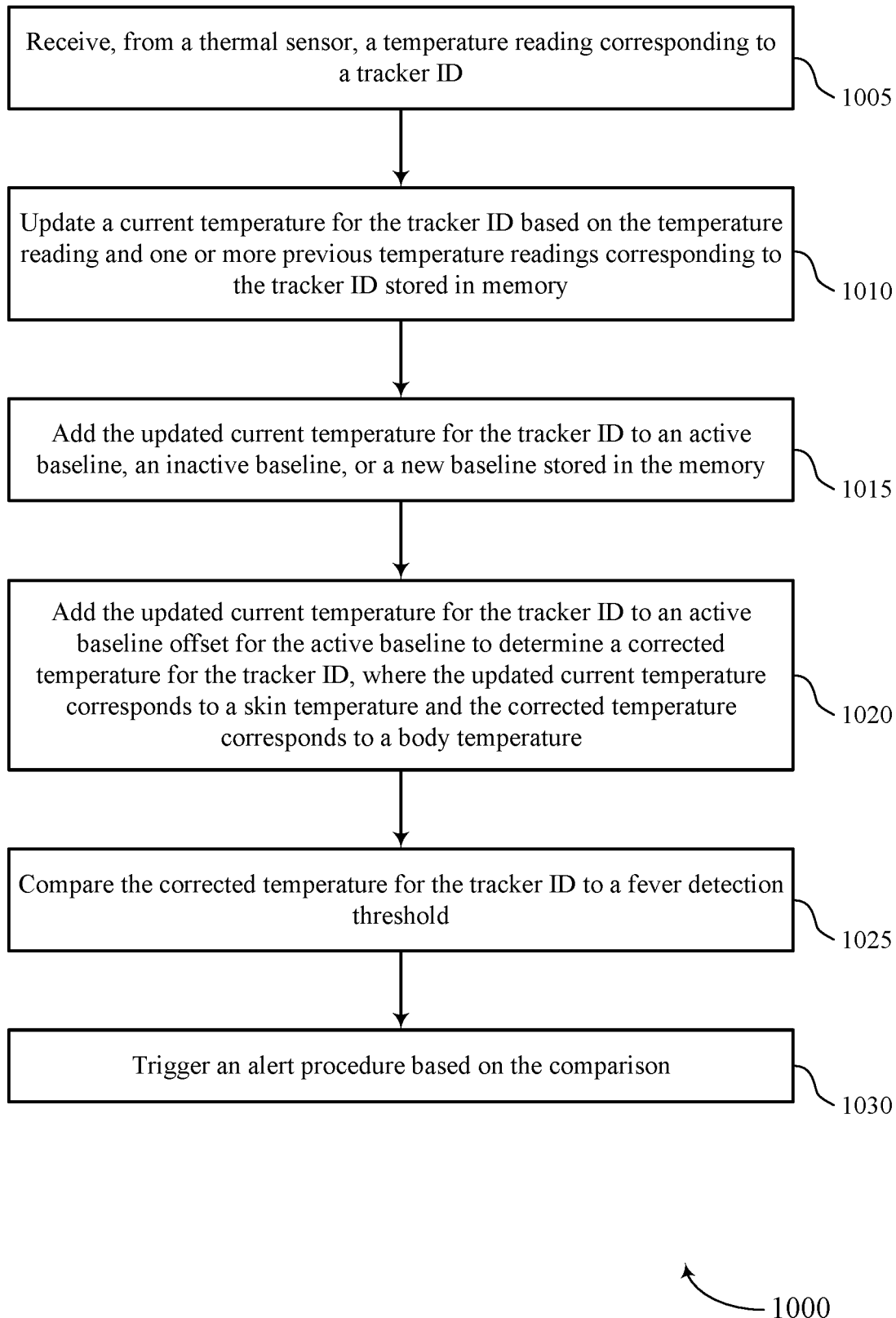

FIG. 10 shows a flowchart illustrating a method 1000 that supports an AI procedure for normalizing thermal skin temperature to body temperature in accordance with aspects of the present disclosure. The operations of method 1000 may be implemented by a processing device or its components as described herein. For example, the operations of method 1000 may be performed by a temperature detection manager as described with reference to FIGS. 5 through 7. The processing device may be an example of a camera, a sensor, a user device, a server (e.g., an application server, a database server, a cloud-based server, a worker server, a server cluster, a virtual machine, a container, or any combination of these or other devices or systems supporting data processing), or any combination thereof. In some examples, a processing device may execute a set of instructions to control the functional elements of the processing device to perform the functions described below. Additionally or alternatively, a processing device may perform aspects of the functions described below using special-purpose hardware.

At 1005, the processing device may receive, from a thermal sensor, a temperature reading corresponding to a tracker ID. The operations of 1005 may be performed according to the methods described herein. In some examples, aspects of the operations of 1005 may be performed by a temperature reading component as described with reference to FIGS. 5 through 7.

At 1010, the processing device may update a current temperature for the tracker ID based on the temperature reading and one or more previous temperature readings corresponding to the tracker ID stored in memory. The operations of 1010 may be performed according to the methods described herein. In some examples, aspects of the operations of 1010 may be performed by a current temperature component as described with reference to FIGS. 5 through 7.

At 1015, the processing device may add the updated current temperature for the tracker ID to an active baseline, an inactive baseline, or a new baseline stored in the memory. The operations of 1015 may be performed according to the methods described herein. In some examples, aspects of the operations of 1015 may be performed by a baseline updating component as described with reference to FIGS. 5 through 7.

At 1020, the processing device may add the updated current temperature for the tracker ID to an active baseline offset for the active baseline to determine a corrected temperature for the tracker ID, where the updated current temperature corresponds to a skin temperature and the corrected temperature corresponds to a body temperature. The operations of 1020 may be performed according to the methods described herein. In some examples, aspects of the operations of 1020 may be performed by a corrected temperature component as described with reference to FIGS. 5 through 7.

At 1025, the processing device may compare the corrected temperature for the tracker ID to a fever detection threshold. The operations of 1025 may be performed according to the methods described herein. In some examples, aspects of the operations of 1025 may be performed by a temperature threshold component as described with reference to FIGS. 5 through 7.

At 1030, the processing device may trigger an alert procedure based on the comparison. The operations of 1030 may be performed according to the methods described herein. In some examples, aspects of the operations of 1030 may be performed by an alert component as described with reference to FIGS. 5 through 7.

A method for temperature detection is described. The method may include receiving, from a thermal sensor, a temperature reading corresponding to a tracker ID, updating a current temperature for the tracker ID based on the temperature reading and one or more previous temperature readings corresponding to the tracker ID stored in memory, adding the updated current temperature for the tracker ID to an active baseline, an inactive baseline, or a new baseline stored in the memory, determining that the updated current temperature for the tracker ID satisfies an alert threshold for the active baseline, and triggering an alert procedure based on determining that the updated current temperature for the tracker ID satisfies the alert threshold.

An apparatus for temperature detection is described. The apparatus may include a processor, memory coupled with the processor, and instructions stored in the memory. The instructions may be executable by the processor to cause the apparatus to receive, from a thermal sensor, a temperature reading corresponding to a tracker ID, update a current temperature for the tracker ID based on the temperature reading and one or more previous temperature readings corresponding to the tracker ID stored in memory, add the updated current temperature for the tracker ID to an active baseline, an inactive baseline, or a new baseline stored in the memory, determine that the updated current temperature for the tracker ID satisfies an alert threshold for the active baseline, and trigger an alert procedure based on determining that the updated current temperature for the tracker ID satisfies the alert threshold.

Another apparatus for temperature detection is described. The apparatus may include means for receiving, from a thermal sensor, a temperature reading corresponding to a tracker ID, updating a current temperature for the tracker ID based on the temperature reading and one or more previous temperature readings corresponding to the tracker ID stored in memory, adding the updated current temperature for the tracker ID to an active baseline, an inactive baseline, or a new baseline stored in the memory, determining that the updated current temperature for the tracker ID satisfies an alert threshold for the active baseline, and triggering an alert procedure based on determining that the updated current temperature for the tracker ID satisfies the alert threshold.

A non-transitory computer-readable medium storing code for temperature detection is described. The code may include instructions executable by a processor to receive, from a thermal sensor, a temperature reading corresponding to a tracker ID, update a current temperature for the tracker ID based on the temperature reading and one or more previous temperature readings corresponding to the tracker ID stored in memory, add the updated current temperature for the tracker ID to an active baseline, an inactive baseline, or a new baseline stored in the memory, determine that the updated current temperature for the tracker ID satisfies an alert threshold for the active baseline, and trigger an alert procedure based on determining that the updated current temperature for the tracker ID satisfies the alert threshold.

Some examples of the method, apparatuses, and non-transitory computer-readable medium described herein may further include operations, features, means, or instructions for adding the temperature reading to a list in the memory corresponding to the tracker ID and including the one or more previous temperature readings corresponding to the tracker ID and removing, from the list in the memory corresponding to the tracker ID, a least recent temperature reading of the one or more previous temperature readings corresponding to the tracker ID based on the list in the memory satisfying a threshold list length.

In some examples of the method, apparatuses, and non-transitory computer-readable medium described herein, updating the current temperature for the tracker ID may include operations, features, means, or instructions for iteratively determining whether a highest temperature reading of the list in the memory corresponds to an outlier value and setting the current temperature for the tracker ID to a highest non-outlier temperature reading of the list in the memory based on the iterative determining.

Some examples of the method, apparatuses, and non-transitory computer-readable medium described herein may further include operations, features, means, or instructions for removing a previous current temperature for the tracker ID from the active baseline, the inactive baseline, or the new baseline based on adding the updated current temperature for the tracker ID to the active baseline, the inactive baseline, or the new baseline.

In some examples of the method, apparatuses, and non-transitory computer-readable medium described herein, adding the updated current temperature for the tracker ID to the active baseline, the inactive baseline, or the new baseline may include operations, features, means, or instructions for comparing the updated current temperature for the tracker ID to a mean value of the active baseline and one or more additional mean values of one or more inactive baselines stored in the memory and adding the updated current temperature for the tracker ID to the active baseline, the inactive baseline of the one or more inactive baselines, or the new baseline based on the comparing.

In some examples of the method, apparatuses, and non-transitory computer-readable medium described herein, triggering the alert procedure may include operations, features, means, or instructions for adding the updated current temperature for the tracker ID to an active baseline offset for the active baseline to determine a corrected temperature for the tracker ID, where the updated current temperature corresponds to a skin temperature and the corrected temperature corresponds to a body temperature, and comparing the corrected temperature for the tracker ID to a fever detection threshold.

Some examples of the method, apparatuses, and non-transitory computer-readable medium described herein may further include operations, features, means, or instructions for determining that the corrected temperature for the tracker ID exceeds the fever detection threshold based on the comparing, setting the corrected temperature for the tracker ID to a temporary value below the fever detection threshold for a configured time duration, receiving, from the thermal sensor, a set of additional temperature readings corresponding to the tracker ID during the configured time duration, and determining whether to execute an alert for the tracker ID based on the set of additional temperature readings corresponding to the tracker ID.

In some examples of the method, apparatuses, and non-transitory computer-readable medium described herein, determining whether to execute the alert for the tracker ID may include operations, features, means, or instructions for determining to execute the alert for the tracker ID based on the set of additional temperature readings corresponding to the tracker ID and transmit a digital indicator, an SMS message, an email message, or a combination thereof indicating the tracker ID, the corrected temperature for the tracker ID, or a combination thereof based on determining to execute the alert for the tracker ID.

Some examples of the method, apparatuses, and non-transitory computer-readable medium described herein may further include operations, features, means, or instructions for comparing the updated current temperature for the tracker ID to a mean value of the active baseline, determining that the updated current temperature for the tracker ID corresponds to an anomalous value for the active baseline based on the comparing, determining a number of anomalous values for the active baseline satisfies a threshold based on the updated current temperature for the tracker ID corresponding to the anomalous value, and deactivating the active baseline based on the number of anomalous values for the active baseline satisfying the threshold.

Some examples of the method, apparatuses, and non-transitory computer-readable medium described herein may further include operations, features, means, or instructions for determining that a threshold time duration has passed since receiving a most recent temperature reading from the thermal sensor and deactivating the active baseline based on the threshold time duration having passed since receiving the most recent temperature reading.

In some examples of the method, apparatuses, and non-transitory computer-readable medium described herein, the updated current temperature for the tracker ID may be added to a first inactive baseline of one or more inactive baselines stored in the memory. Some examples of the method, apparatuses, and non-transitory computer-readable medium described herein may further include operations, features, means, or instructions for determining that a threshold number of current temperatures have been added to the first inactive baseline more recently than a most recent current temperature has been added to the active baseline, deactivating the active baseline based on the threshold number of current temperatures having been added to the first inactive baseline more recently than the most recent current temperature has been added to the active baseline, and activating the first inactive baseline based on the threshold number of current temperatures having been added to the first inactive baseline more recently than the most recent current temperature has been added to the active baseline.

Some examples of the method, apparatuses, and non-transitory computer-readable medium described herein may further include operations, features, means, or instructions for identifying, at an optical camera, a first set of pixels corresponding to a face, identifying, at the thermal sensor, a second set of pixels corresponding to the face based on an alignment between the optical camera and the thermal sensor, and detecting, at the thermal sensor, a set of temperature readings from the second set of pixels for a frame, where the temperature reading corresponding to the tracker ID may be received based on the set of temperature readings.

Some examples of the method, apparatuses, and non-transitory computer-readable medium described herein may further include operations, features, means, or instructions for detecting, at the optical camera, a body based on a motion detection procedure and a first neural network, where the first set of pixels corresponding to the face may be identified based on the detected body and a second neural network, and assigning, in the memory, the tracker ID to the body.

In some examples of the method, apparatuses, and non-transitory computer-readable medium described herein, the active baseline may be a first active baseline. Some examples of the method, apparatuses, and non-transitory computer-readable medium described herein may further include operations, features, means, or instructions for determining that the tracker ID corresponds to the first active baseline of a set of active baselines based on a direction that the body entered a view of the optical camera.

In some examples of the method, apparatuses, and non-transitory computer-readable medium described herein, the body may be detected in a first frame of the optical camera. Some examples of the method, apparatuses, and non-transitory computer-readable medium described herein may further include operations, features, means, or instructions for detecting, at the optical camera, the body in a second frame of the optical camera and maintaining, in the memory, the tracker ID assigned to the body based on detecting the body in the second frame.

Some examples of the method, apparatuses, and non-transitory computer-readable medium described herein may further include operations, features, means, or instructions for receiving, from the optical camera, an image of the face and storing, in the memory, the image of the face and a reference to the tracker ID.

Some examples of the method, apparatuses, and non-transitory computer-readable medium described herein may further include operations, features, means, or instructions for determining a distance from the face to the thermal sensor and adjusting the set of temperature readings based on the determined distance.

In some examples of the method, apparatuses, and non-transitory computer-readable medium described herein, detecting the set of temperature readings from the second set of pixels for the frame may include operations, features, means, or instructions for identifying, from the second set of pixels, one or more first pixels associated with an optical region of the face, one or more second pixels associated with a nasal region of the face, one or more third pixels associated with a forehead region of the face, or a combination thereof, where the set of temperature readings may be detected from the one or more first pixels, the one or more second pixels, the one or more third pixels, or a combination thereof, and the set of temperature readings include thermal skin temperature readings for the face.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein but is to be accorded the broadest scope consistent with the principles and novel features disclosed herein.

What is claimed is:

1. A method for temperature detection, comprising:
   receiving, from a thermal sensor, a temperature reading corresponding to a tracker identifier;
   adding the temperature reading to a list in memory corresponding to the tracker identifier and comprising one or more previous temperature readings corresponding to the tracker identifier;
   removing, from the list in the memory corresponding to the tracker identifier, a least recent temperature reading of the one or more previous temperature readings corresponding to the tracker identifier based at least in part on the list in the memory satisfying a threshold list length;
   updating a current temperature for the tracker identifier based at least in part on the temperature reading and the one or more previous temperature readings in the list corresponding to the tracker identifier stored in the memory;
   adding the updated current temperature for the tracker identifier to an active baseline, an inactive baseline, or a new baseline stored in the memory;
   determining that the updated current temperature for the tracker identifier satisfies an alert threshold for the active baseline; and triggering an alert procedure based at least in part on determining that the updated current temperature for the tracker identifier satisfies the alert threshold.

2. The method of claim 1, wherein updating the current temperature for the tracker identifier comprises:
   iteratively determining whether a highest temperature reading of the list in the memory corresponds to an outlier value; and
   setting the current temperature for the tracker identifier to a highest non-outlier temperature reading of the list in the memory based at least in part on the iterative determining.

3. The method of claim 1, further comprising:
   removing a previous current temperature for the tracker identifier from the active baseline, the inactive baseline, or the new baseline based at least in part on adding the updated current temperature for the tracker identifier to the active baseline, the inactive baseline, or the new baseline.

4. The method of claim 1, wherein adding the updated current temperature for the tracker identifier to the active baseline, the inactive baseline, or the new baseline comprises:
   comparing the updated current temperature for the tracker identifier to a mean value of the active baseline and one or more additional mean values of one or more inactive baselines stored in the memory; and
   adding the updated current temperature for the tracker identifier to the active baseline, the inactive baseline of the one or more inactive baselines, or the new baseline based at least in part on the comparing.

5. The method of claim 1, wherein triggering the alert procedure comprises:
   adding the updated current temperature for the tracker identifier to an active baseline offset for the active baseline to determine a corrected temperature for the tracker identifier, wherein the updated current temperature corresponds to a skin temperature and the corrected temperature corresponds to a body temperature; and
   comparing the corrected temperature for the tracker identifier to a fever detection threshold.

6. The method of claim 5, further comprising:
   determining that the corrected temperature for the tracker identifier exceeds the fever detection threshold based at least in part on the comparing;
   setting the corrected temperature for the tracker identifier to a temporary value below the fever detection threshold for a configured time duration;
   receiving, from the thermal sensor, a plurality of additional temperature readings corresponding to the tracker identifier during the configured time duration; and
   determining whether to execute an alert for the tracker identifier based at least in part on the plurality of additional temperature readings corresponding to the tracker identifier.

7. The method of claim 6, wherein determining whether to execute the alert for the tracker identifier comprises:
   determining to execute the alert for the tracker identifier based at least in part on the plurality of additional temperature readings corresponding to the tracker identifier; and
   transmitting a digital indicator, a short message service message, an email message, or a combination thereof indicating the tracker identifier, the corrected temperature for the tracker identifier, or a combination thereof based at least in part on determining to execute the alert for the tracker identifier.

8. The method of claim 1, further comprising:
   comparing the updated current temperature for the tracker identifier to a mean value of the active baseline;
   determining that the updated current temperature for the tracker identifier corresponds to an anomalous value for the active baseline based at least in part on the comparing;
   determining a number of anomalous values for the active baseline satisfies a threshold based at least in part on the updated current temperature for the tracker identifier corresponding to the anomalous value; and
   deactivating the active baseline based at least in part on the number of anomalous values for the active baseline satisfying the threshold.

9. The method of claim 1, further comprising:
   determining that a threshold time duration has passed since receiving a most recent temperature reading from the thermal sensor; and
   deactivating the active baseline based at least in part on the threshold time duration having passed since receiving the most recent temperature reading.

10. The method of claim 1, wherein the updated current temperature for the tracker identifier is added to a first inactive baseline of one or more inactive baselines stored in the memory, the method further comprising:
    determining that a threshold number of current temperatures have been added to the first inactive baseline more recently than a most recent current temperature has been added to the active baseline;
    deactivating the active baseline based at least in part on the threshold number of current temperatures having been added to the first inactive baseline more recently than the most recent current temperature has been added to the active baseline; and
    activating the first inactive baseline based at least in part on the threshold number of current temperatures having been added to the first inactive baseline more recently than the most recent current temperature has been added to the active baseline.

11. The method of claim 1, further comprising:
    identifying, at an optical camera, a first set of pixels corresponding to a face;
    identifying, at the thermal sensor, a second set of pixels corresponding to the face based at least in part on an alignment between the optical camera and the thermal sensor; and
    detecting, at the thermal sensor, a set of temperature readings from the second set of pixels for a frame, wherein the temperature reading corresponding to the tracker identifier is received based at least in part on the set of temperature readings.

12. The method of claim 11, further comprising:
    detecting, at the optical camera, a body based at least in part on a motion detection procedure and a first neural network, wherein the first set of pixels corresponding to the face is identified based at least in part on the detected body and a second neural network; and
    assigning, in the memory, the tracker identifier to the body.

13. The method of claim 12, wherein the active baseline comprises a first active baseline, the method further comprising:
    determining that the tracker identifier corresponds to the first active baseline of a plurality of active baselines based at least in part on a direction that the body entered a view of the optical camera.

14. The method of claim 12, wherein the body is detected in a first frame of the optical camera, the method further comprising:
   detecting, at the optical camera, the body in a second frame of the optical camera; and
   maintaining, in the memory, the tracker identifier assigned to the body based at least in part on detecting the body in the second frame.

15. The method of claim 12, further comprising:
   receiving, from the optical camera, an image of the face; and
   storing, in the memory, the image of the face and a reference to the tracker identifier.

16. The method of claim 11, further comprising:
   determining a distance from the face to the thermal sensor; and
   adjusting the set of temperature readings based at least in part on the determined distance.

17. The method of claim 11, wherein detecting the set of temperature readings from the second set of pixels for the frame comprises:
   identifying, from the second set of pixels, one or more first pixels associated with an optical region of the face, one or more second pixels associated with a nasal region of the face, one or more third pixels associated with a forehead region of the face, or a combination thereof, wherein the set of temperature readings are detected from the one or more first pixels, the one or more second pixels, the one or more third pixels, or a combination thereof, and the set of temperature readings comprise thermal skin temperature readings for the face.

18. An apparatus for temperature detection, comprising:
   a processor;
   memory coupled with the processor; and
   instructions stored in the memory and executable by the processor to cause the apparatus to:
      receive, from a thermal sensor, a temperature reading corresponding to a tracker identifier;
      add the temperature reading to a list in the memory corresponding to the tracker identifier and comprising one or more previous temperature readings corresponding to the tracker identifier;
      remove, from the list in the memory corresponding to the tracker identifier, a least recent temperature reading of the one or more previous temperature readings corresponding to the tracker identifier based at least in part on the list in the memory satisfying a threshold list length;
      update a current temperature for the tracker identifier based at least in part on the temperature reading and the one or more previous temperature readings in the list corresponding to the tracker identifier stored in the memory;
      add the updated current temperature for the tracker identifier to an active baseline, an inactive baseline, or a new baseline stored in the memory;
      determine that the updated current temperature for the tracker identifier satisfies an alert threshold for the active baseline; and
      trigger an alert procedure based at least in part on determining that the updated current temperature for the tracker identifier satisfies the alert threshold.

19. A non-transitory computer-readable medium storing code for temperature detection, the code comprising instructions executable by a processor to:
   receive, from a thermal sensor, a temperature reading corresponding to a tracker identifier;
   add the temperature reading to a list in memory corresponding to the tracker identifier and comprising one or more previous temperature readings corresponding to the tracker identifier;
   remove, from the list in the memory corresponding to the tracker identifier, a least recent temperature reading of the one or more previous temperature readings corresponding to the tracker identifier based at least in part on the list in the memory satisfying a threshold list length;
   update a current temperature for the tracker identifier based at least in part on the temperature reading and the one or more previous temperature readings in the list corresponding to the tracker identifier stored in the memory;
   add the updated current temperature for the tracker identifier to an active baseline, an inactive baseline, or a new baseline stored in the memory;
   determine that the updated current temperature for the tracker identifier satisfies an alert threshold for the active baseline; and
   trigger an alert procedure based at least in part on determining that the updated current temperature for the tracker identifier satisfies the alert threshold.

* * * * *